(12) United States Patent
Tokuda et al.

(10) Patent No.: US 8,820,139 B2
(45) Date of Patent: Sep. 2, 2014

(54) PARTICULATE MATTER DETECTION DEVICE

(75) Inventors: Masahiro Tokuda, Nagoya (JP); Takashi Egami, Nagoya (JP); Takeshi Sakuma, Nagoya (JP); Atsuo Kondo, Nagoya (JP); Masanobu Miki, Wako (JP); Keizo Iwama, Wako (JP); Tatsuya Okayama, Wako (JP)

(73) Assignees: NGK Insulators, Ltd., Nagoya (JP); Honda Motor Co., Ltd., Minato-Ku (JP)

( * ) Notice: Subject to any disclaimer, the term of this patent is extended or adjusted under 35 U.S.C. 154(b) by 330 days.

(21) Appl. No.: 13/216,625

(22) Filed: Aug. 24, 2011

(65) Prior Publication Data

US 2012/0047991 A1    Mar. 1, 2012

(30) Foreign Application Priority Data

Aug. 26, 2010   (JP) .................................. 2010-189924

(51) Int. Cl.
*G01N 7/00* (2006.01)
(52) U.S. Cl.
USPC ......................................................... 73/23.33
(58) Field of Classification Search
USPC ................................... 73/23.33, 28.01, 23.31
See application file for complete search history.

(56) References Cited

U.S. PATENT DOCUMENTS

| 2010/0000863 A1 | 1/2010 | Kondo et al. | |
| 2010/0229629 A1* | 9/2010 | Egami et al. | 73/28.01 |
| 2011/0163761 A1* | 7/2011 | Yokoi et al. | 324/601 |

FOREIGN PATENT DOCUMENTS

| JP | 63-106548 A1 | 5/1988 |
| JP | 3097932 B2 | 10/2000 |
| JP | 2005-114357 A1 | 4/2005 |
| JP | 2006-058196 A1 | 3/2006 |
| JP | 2009-186278 A1 | 8/2009 |
| JP | 2010-032488 A1 | 2/2010 |

OTHER PUBLICATIONS

Japanese Office Action (Application No. 2010-189924) dated Jan. 28, 2014 (with partial English translation).

* cited by examiner

*Primary Examiner* — Hezron E Williams
*Assistant Examiner* — David Z Huang
(74) *Attorney, Agent, or Firm* — Burr & Brown, PLLC

(57) ABSTRACT

A particulate matter detection device of the present invention includes a plate-like element base material, and a pair of measurement electrodes arranged in the element base material, each of the measurement electrodes is a combteeth-like electrode including a plurality of planarly arranged combteeth portions, and a comb spine portion which connects the plurality of combteeth portions of each of the measurement electrodes to one another at one end of each of the plurality of combteeth portions, the combteeth portions of the measurement electrodes are arranged to engage with each other with a space being left therebetween, and the comb spine portion of at least one of the measurement electrodes is covered with a comb spine covering portion made of a dielectric material.

11 Claims, 12 Drawing Sheets

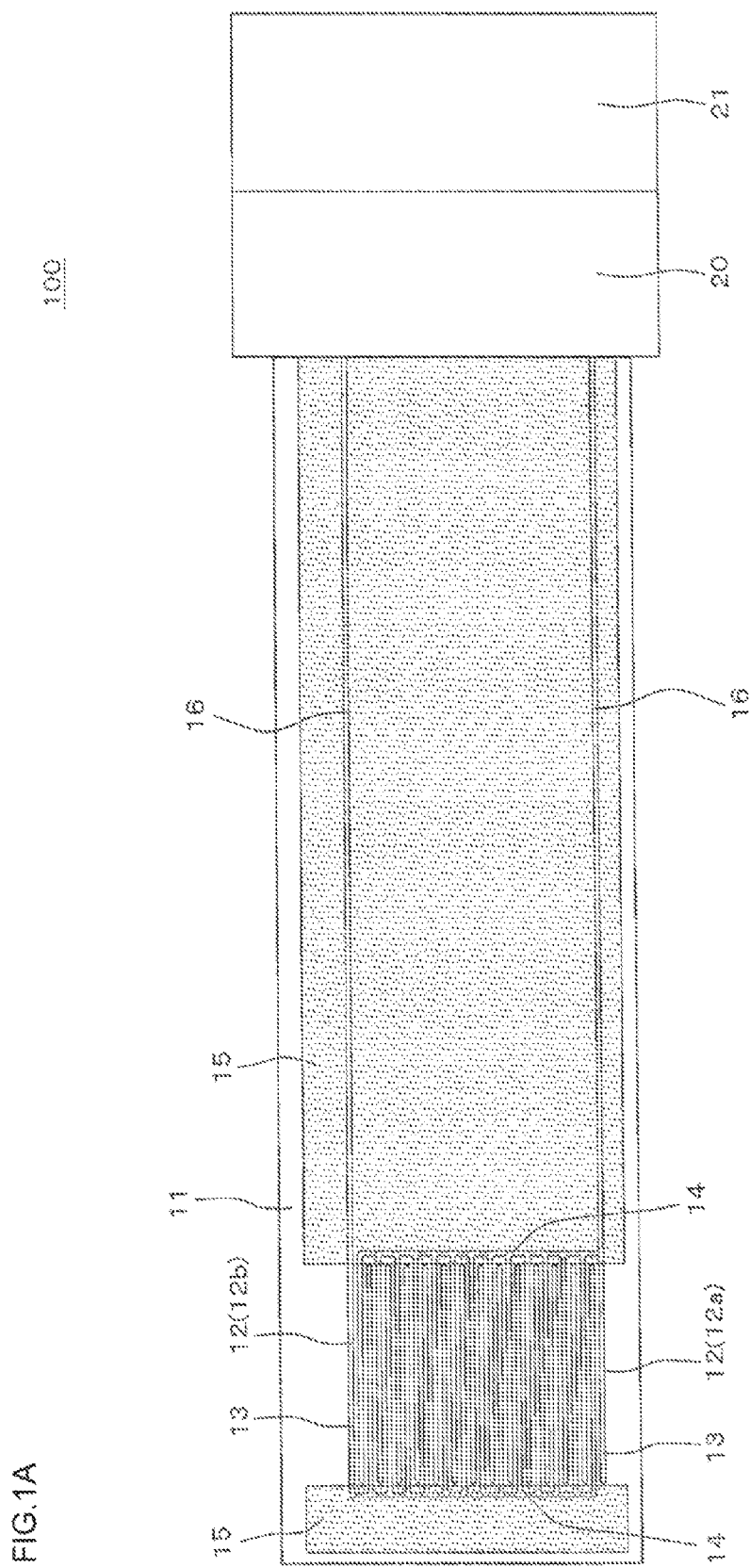

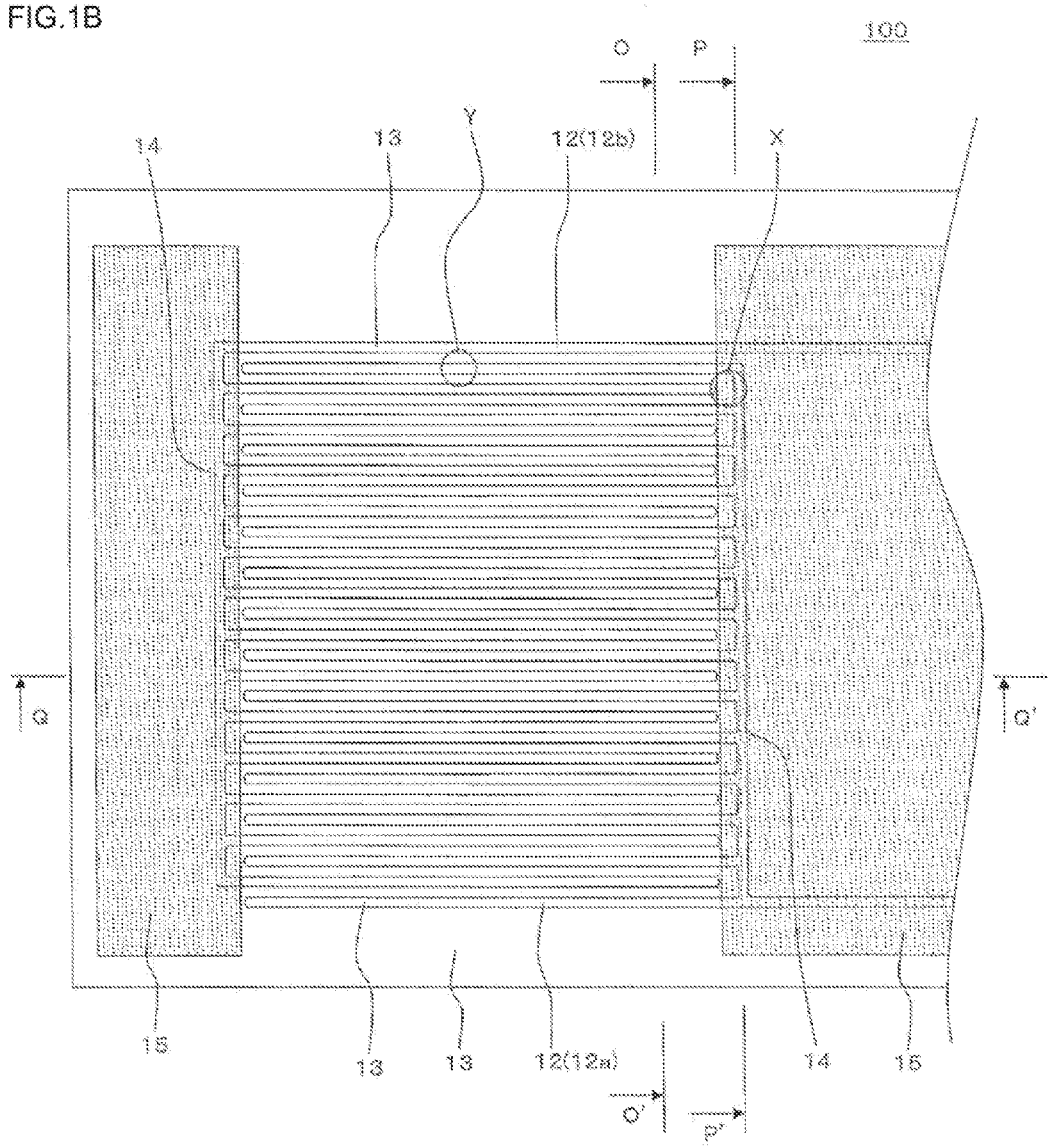

PARTICULATE MATTER DETECTION DEVICE

BACKGROUND OF THE INVENTION

1. Field of the Invention

The present invention relates to a particulate matter detection device, and more particularly, it relates to a particulate matter detection device having a high measurement sensitivity and a high measurement accuracy.

2. Description of the Related Art

A flue exhaust gas or a diesel engine exhaust gas includes a particulate matter (PM) such as soot, which has been a cause for air pollution. For the purpose of removing the particulate matter, a filter (a diesel particulate filter: DPF) made of a ceramic material or the like has widely been used. The DPF made of the ceramic material can be used for a long period of time, but defects such as cracks or melting damages due to thermal deterioration or the like might be generated, and a micro amount of the particulate matter might leak. When such defects are generated, from the viewpoint of the prevention of the air pollution, it is remarkably important to immediately detect the generation of the defects, thereby recognizing the abnormality of a device.

As a method of detecting the generation of such defects, there is disclosed a method of disposing a particulate matter detection device on a downstream side of the DPF (e.g., see Patent Documents 1 and 2).

For example, the particulate matter detection device disclosed in Patent Document 1 includes a detection device main body which includes a through hole formed in one end thereof and which is long in one direction, and at least a pair of electrodes embedded in a wall which forms this through hole and covered with a dielectric material. It is possible to electrically adsorb, by the wall surface of this through hole, a charged particulate matter included in a fluid flowing into the through hole, or a particulate matter charged by discharge which occurs in the through hole when a voltage is applied across the pair of electrodes and included in the fluid flowing into the through hole. When a change of electric characteristics of the wall which forms the through hole is measured, it is possible to detect a mass of the particulate matter adsorbed by the wall surface of the through hole.

Consequently, the conventional particulate matter detection device allows the particulate matter included in a measurement target gas to adhere to and around the pair of electrodes which are sensors, and measures the change of, the electric characteristics between the pair of electrodes, to detect the particulate matter in the measurement target gas.

Moreover, for example, as shown in FIG. 5 of Patent Document 2, as the pair of electrodes which are sensors for measurement, there are suggested a pair of electrodes which are branched into a plurality of electrodes, respectively, so that the branched electrodes face each other and a plurality of facing portions are present. When such electrodes are used and, for example, an electrostatic capacity is measured as electric characteristics between the pair of electrodes, a measurement sensitivity of the electrodes can be enhanced.

PRIOR ART DOCUMENTS

Patent Document

[Patent Document 1] JP-A-2009-186278
[Patent Document 2] JP-A-2010-32488

SUMMARY OF THE INVENTION

Even in such a conventional particulate matter detection device, however, there has been a problem that a measurement sensitivity of the device is still not satisfactory. In particular, regulations on the removal of a particulate matter from an exhaust gas tend to be strengthened worldwide, and there has been demanded the development of a detection device which can more accurately detect a particulate matter.

The present invention has been developed in view of the above problem, and an object thereof is to provide a particulate matter detection device having a high measurement sensitivity and a high measurement accuracy.

The present inventors have found that when a pair of electrodes are formed into a combteeth-like shape, respectively, and combteeth portions are arranged to engage with each other, a measurement sensitivity of a detection device can be enhanced to a certain degree, but the present inventors further have performed investigations on the development of a particulate matter detection device having a higher measurement sensitivity and an excellent measurement accuracy.

In consequence, when the electrodes are formed into the combteeth-like shape as described above, a space between the electrodes can be narrowed, and the space between the electrodes (i.e., a space between combteeth portions) can be uniform. Therefore, the measurement accuracy of the detection device can be enhanced to a certain degree, but from the viewpoint of the manufacturing of the electrodes, it is remarkably difficult to obtain all uniform spaces even among a portion (a comb spine portion) which connects the ends of the combteeth portions to one another and the combteeth portions which face this connecting portion. It has become clear that the space between the comb spine portion and each combteeth portion is a factor which disturbs the enhancement of the measurement accuracy of the device.

The present inventors have found that when the above comb spine portions of the combteeth-like electrodes are covered with a dielectric material, the above object can be achieved, whereby the present invention has been completed. According to the present invention, a particulate matter detection device is provided as follows.

According to a first as aspect of the present invention, a particulate matter detection device is provided, the particulate matter detection device comprising: a plate-like element base material; a pair of measurement electrodes arranged in the element base material; characteristics measurement means for measuring electric characteristics between the pair of measurement electrodes; and particulate matter amount calculation means for obtaining an amount of a particulate matter collected in and around the pair of measurement electrodes on the basis of a change amount of the electric characteristics measured by the characteristics measurement means, wherein the measurement electrodes constituting the pair of measurement electrodes are combteeth-like electrodes each including a plurality of planarly arranged combteeth portions, and a comb spine portion which connects the plurality of combteeth portions of each of the measurement electrodes to one another at one end of each of the plurality of combteeth portions, the combteeth portions of the measurement electrodes are arranged to engage with each other with a space being left therebetween, and the comb spine portion of at least one of the measurement electrodes is covered with a comb spine covering portion made of a dielectric material.

According to a second aspect of the present invention, the particulate matter detection device according to the first aspect is provided, wherein the comb spine covering portion covers the comb spine portion of the one measurement electrode as well as a tip portion of each of the combteeth portions of the other measurement electrode arranged to engage with each other with the space being left therebetween.

According to a third aspect of the present invention, the particulate matter detection device according to the first aspect is provided, wherein the comb spine covering portion covers the comb spine portion of the one measurement electrode so that the comb spine covering portion abuts on a tip portion of each of the combteeth portions of the other measurement electrode arranged so as to engage with each other with the space being left therebetween.

According to a fourth aspect of the present invention, the particulate matter detection device according to any one of the first through third aspects is provided, wherein at least part of the surfaces of the pair of measurement electrodes is covered with an electrode protective film having a smaller thickness than the comb spine covering portion.

According to a fifth aspect of the present invention, the particulate matter detection device according to any one of the first through fourth aspects is provided, wherein the element base material is a device main body which includes at least one through hole formed in one end thereof and which is long in one direction, the pair of measurement electrodes are arranged on an inner side surface of one wall which forms the through hole or in the wall, and the comb spine covering portion is formed by a wall extending vertically from the wall on which the pair of measurement electrodes are arranged, among the walls which form the through hole.

According to a sixth aspect of the present invention, the particulate matter detection device according to the fifth aspect is provided, wherein the measurement electrodes are arranged so that a direction in which combteeth of the combteeth portions of the measurement electrodes extend is orthogonal to a direction in which the through hole extends through the element base material.

According to a seventh aspect of the present invention, the particulate matter detection device according to any one of the first through sixth aspects is provided, wherein a gas including the particulate matter as a detection target is passed through the measurement electrodes in a direction which is orthogonal to the direction in which the combteeth of the combteeth portions of the measurement electrodes extend, to detect the particulate matter.

That is, in a particulate matter detection device of the present invention according to the first aspect, when a comb spine portion as a factor which lowers a measurement accuracy is covered with a comb spine covering portion, the comb spine portion loses a function of a measurement portion, so that this comb spine portion does not adversely affect a measured value. That is, a particulate matter can more accurately be detected. Moreover, when the comb spine portion is covered in this manner, an initial value of electric characteristics measured by a pair of measurement electrodes (e.g., a value of an electrostatic capacity in a state where any particulate matter does not adhere) becomes large. Therefore, the particulate matter detection device is remarkably effective in a case where on-board diagnosis (OBD), i.e., self fault diagnosis of the device using this initial value is performed.

Moreover, in the particulate matter detection device of the invention according to the second and third aspects, a substantial measurement surface is a portion where the combteeth portions are engaged with each other, and a space between the measurement electrodes becomes more uniform, whereby remarkably accurate measurement can be performed.

Furthermore, in the particulate matter detection device of the invention according to the fourth aspect, at least part of the surfaces of the pair of measurement electrodes is covered with an electrode protective film which has a smaller thickness than the comb spine covering portion, whereby the corrosion of the combteeth portions can be prevented. Moreover, while the combteeth portions having a function of measurement surfaces are covered with the electrode protective film, the comb spine portion is covered with the comb spine covering portion having a larger thickness. In consequence, owing to the electrode protective film combined with the comb spine covering portion, the measurement of the particulate matter included in an exhaust gas can more satisfactorily be performed.

Furthermore, in the particulate matter detection device of the invention according to the fifth aspect, an element base material is a device main body which includes at least a through hole formed in one end thereof and which is long in one direction, and the pair of measurement electrodes are arranged on the inner side surface of one wall which forms the through hole or in the wall. Moreover, the comb spine covering portion is formed by a wall extending vertically from the wall on which the pair of measurement electrodes are arranged, among the walls which form the through hole. Therefore, it is not necessary to separately dispose the comb spine covering portion, which can simplify the constitution of the detection device. Moreover, in the element base material having the above constitution, a measurement target gas such as the exhaust gas is passed through the through hole, whereby the particulate matter included in the measurement target gas can satisfactorily be detected.

Additionally, in the particulate matter detection device of the invention according to the sixth aspect, with respect to the flow of the gas passing through the through hole, a space between the combteeth portions becomes constant, whereby the accurate measurement can be performed.

Furthermore, in the particulate matter detection device of the invention according to the seventh aspect, the comb spine covering portion disposed outside the combteeth portions forms a passage (a through channel) of the gas, whereby the particulate matter can more satisfactorily be detected. It is to be noted that the invention according to the first through seventh aspects of the present invention correspond to the invention as described above.

BRIEF DESCRIPTION OF THE DRAWINGS

FIG. 1A is a plan view schematically showing an embodiment of a particulate matter detection device of the present invention;

FIG. 1B is an enlarged plan view showing an enlarged part where a pair of measurement electrodes of the particulate matter detection device shown in FIG. 1A are arranged;

DETAILED DESCRIPTION OF THE INVENTION

Figure 1C:
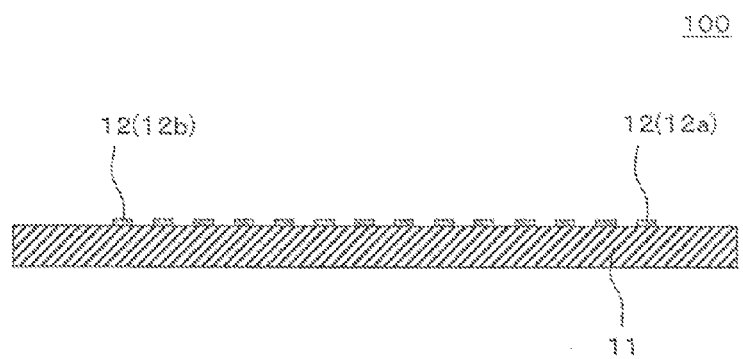
FIG. 1C is an exemplary diagram showing a section cut along the O-O' line of FIG. 1B.

Hereinafter, a mode for carrying out the present invention will specifically be described, but it should be understood that the present invention is not limited to the following embodiments and changes, modifications and the like of design can appropriately be added thereto on the basis of the ordinary knowledge of a person skilled in the art without departing from the scope of the present invention.

[1] Particulate Matter Detection Device:

As shown in FIG. 1A to FIG. 1E, an embodiment of a particulate matter detection device of the present invention is a particulate matter detection device 100 including a plate-like element base material 11; a pair of measurement electrodes 12 (12a and 12b) arranged in the element base material 11; characteristics measurement means 20 for measuring electric characteristics between the pair of measurement electrodes 12a and 12b; and particulate matter amount calculation means 21 for obtaining the amount of a particulate matter collected in and around the pair of measurement electrodes 12a and 12b on the basis of a change amount of the electric characteristics measured by the characteristics measurement means 20.

Figure 1D:
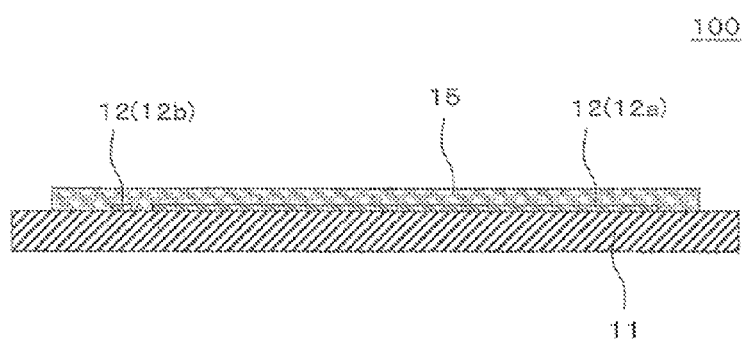
FIG. 1D is an exemplary diagram showing a section cut along the P-P' line of FIG. 1B.
Figure 1E:
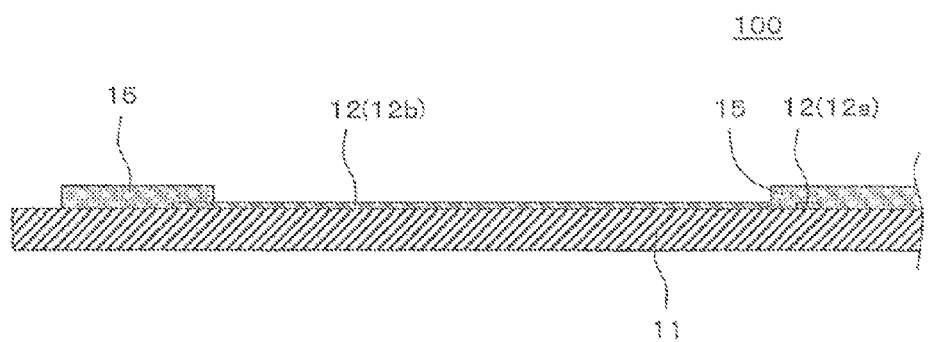
FIG. 1E is an exemplary diagram showing a section cut along the Q-Q' line of FIG. 1B.

Here, FIG. 1A is a plan view schematically showing the embodiment of the particulate matter detection device of the present invention, and FIG. 1B is an enlarged plan view showing an enlarged part where a pair of measurement electrodes of the particulate matter detection device shown in FIG. 1A are arranged. Moreover, FIG. 1C is an exemplary diagram showing a section cut along the O-O' line of FIG. 1B, FIG. 1D is an exemplary diagram showing a section cut along the P-P' line of FIG. 1B, and FIG. 1E is an exemplary diagram showing a section cut along the Q-Q' line of FIG. 1B. In the particulate matter detection device 100 shown in FIG. 1A and FIG. 1B, on the side of one tip of the plate-like element base material 11 which is long in one direction, the pair of measurement electrodes 12a and 12b are arranged, and via a measurement wire 16 extending from the measurement electrodes 12a and 12b, the characteristics measurement means 20 and the particulate matter amount calculation means 21 arranged in the other end of the element base material 11 are electrically connected to the measurement electrodes 12a and 12b.

The particulate matter detection device 100 of the present embodiment allows the particulate matter included in a gas as a measurement target to adhere to and around the pair of measurement electrodes 12a and 12b (collects the particulate matter), and the device measures a change of the electric characteristics between the pair of measurement electrodes 12a and 12b by the characteristics measurement means 20. Furthermore, it is possible to obtain the amount (e.g., a mass) of the collected particulate matter by the particulate matter amount calculation means 21 on the basis of the change amount of the electric characteristics measured by the characteristics measurement means 20. In consequence, the particulate matter detection device 100 of the present embodiment is installed and used in a through channel through which an exhaust gas or the like passes, whereby the particulate matter included in the exhaust gas can be detected.

Moreover, the measurement electrodes 12a and 12b constituting the pair of measurement electrodes 12 of the particulate matter detection device 100 of the present embodiment are combteeth-like electrodes each including a plurality of planarly arranged combteeth portions 13, and a comb spine portion 14 which connects the plurality of combteeth portions 13 of the measurement electrode 12a or 12b to one another at one end of each of the plurality of combteeth portions, and the combteeth portions 13 of the measurement electrodes 12a and 12b are arranged to engage with each other with a space being left therebetween. In such a constitution, it is possible to obtain a long (wide) part where the pair of measurement electrodes 12a and 12b are arranged to face each other, whereby a more accurately measured value can be obtained.

Moreover, when the combteeth-like measurement electrodes are used as described above, a space between the electrodes can be narrowed, and mutual spaces of the electrodes (i.e., spaces among comb teeth portions) can be made uniform, so that a measurement sensitivity can be enhanced. For example, when the electric characteristics to be measured are an electrostatic capacity and the space between the electrodes is narrowed and made uniform, it is possible to accurately read a change in a case where the particulate matter adheres between the electrodes, and it is possible to enhance the measurement sensitivity of the detection device.

When the combteeth-like measurement electrodes are used as described above, however, as shown in FIG. 1B, from the viewpoint of manufacturing, it is remarkably difficult to make uniform all spaces even among the comb spine portion 14 of the one measurement electrode (e.g., the measurement electrode 12a) and the combteeth portions 13 of the other measurement electrode (e.g., the measurement electrode 12b) (e.g., a part shown as a region X in FIG. 1B). Specifically, if a space where the combteeth portions 13 are arranged to engage with each other (e.g., a part shown as a region Y in FIG. 1B) and the space in the region X do not have a uniform size and a portion having a different size is present in the space between the measurement electrodes as in the region X, a measurement accuracy of the detection device relatively lowers.

To solve the problem, in the particulate matter detection device 100 of the present embodiment, the comb spine portion 14 of at least one of the measurement electrodes 12 is covered with a comb spine covering portion 15 made of a dielectric material. In consequence, if the space between the pair of measurement electrodes 12 becomes non-uniform, the spaces among the comb spine portion 14 of the one measurement electrode 12 and the combteeth portions 13 of the other measurement electrode 12 (e.g., the region X) are hidden behind the comb spine covering portion 15. It becomes possible to effectively utilize, as the measurement surface, the part which has a uniform space between the electrodes and in which the combteeth portions 13 are engaged with each other.

According to such a constitution, for example, an initial value of an electrostatic capacity as the electric characteristics measured by the pair of measurement electrodes (i.e., the value of the electrostatic capacity in a state where any particulate matter does not adhere) can be raised, and the measurement sensitivity of the device can be enhanced. When the same amount of the particulate matter is detected, the change amount of the electric characteristics can be increased. Furthermore, since the space between the electrodes becomes uniform in the whole measurement surface, the measurement accuracy can be enhanced.

In the particulate matter detection device of the present embodiment, when the comb spine covering portion covers the comb spine portion of at least one of the measurement electrodes, a constant measurement sensitivity enhancement effect can be obtained. However, as shown in FIG. 1B, both the comb spine portions 14 of the pair of measurement electrodes 12a and 12b are preferably covered with the comb spine covering portions 15. In consequence, the only part where the combteeth portions 13 are engaged with each other substantially becomes the measurement surface, and the space between the measurement electrodes becomes more uniform, whereby the remarkably accurate measurement can be performed.

It is to be noted that when the particulate matter is detected by using the particulate matter detection device of the present embodiment, the gas including the particulate matter as a detection target is preferably allowed to flow in a direction which is orthogonal to a direction in which combteeth of the combteeth portions of the measurement electrodes extend, to detect the particulate matter. When the particulate matter is detected by such a method, the particulate matter satisfactorily adheres to and around the pair of measurement electrodes, and the accurate measurement can be performed.

Figure 2:
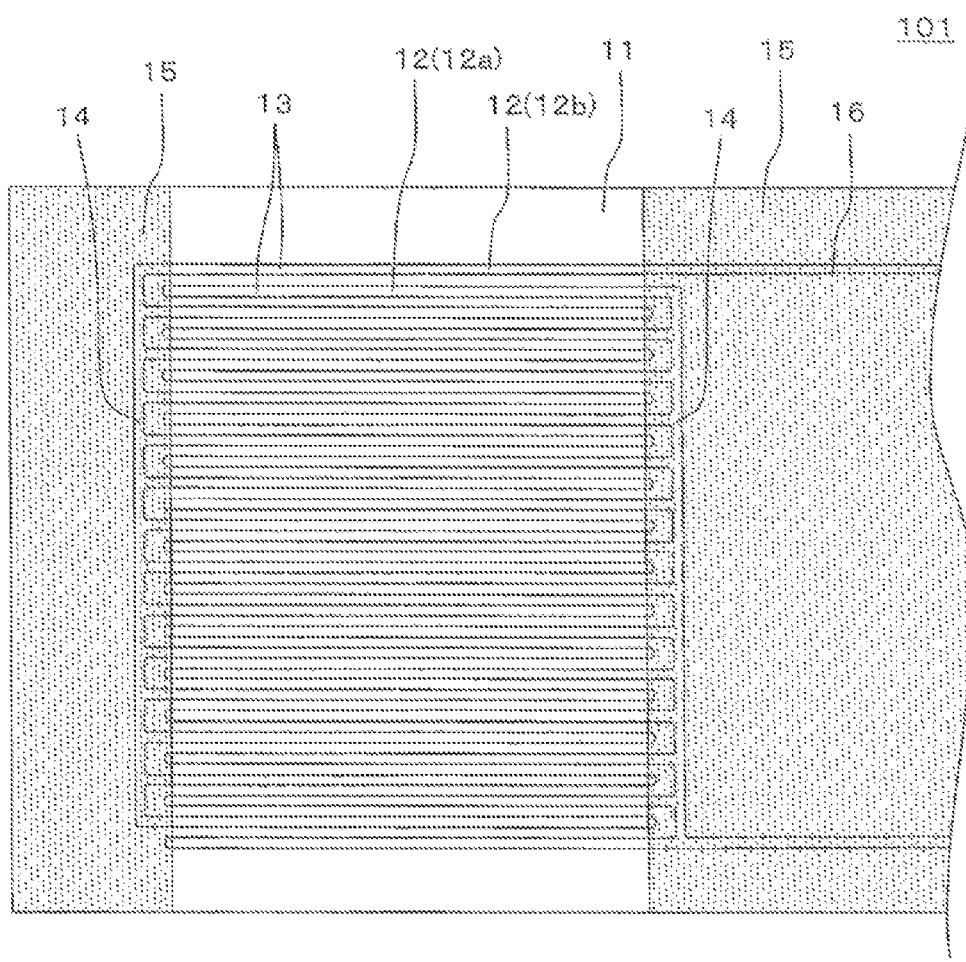
FIG. 2 is an enlarged plan view showing an enlarged part where a pair of measurement electrodes are arranged in another embodiment of the particulate matter detection device of the present invention.

As described above, the comb spine covering portion may cover the comb spine portion of at least one of the measurement electrodes. However, as shown in FIG. 2, the comb spine covering portion 15 preferably covers tip portions of the combteeth portions 13 of the other measurement electrode (e.g., the measurement electrode 12b) arranged to engage with each other with the space being left therebetween as well as the comb spine portion 14 of the one measurement electrode (e.g., the measurement electrode 12a). It is to be noted that FIG. 2 shows an example where the tip portions of the combteeth portions 13 of the one measurement electrode 12a as well as the comb spine portion 14 of the other measurement electrode 12b are covered with the comb spine covering portion 15.

In consequence, when the comb spine covering portion 15 is disposed to cover the tip portions of the combteeth portions 13 arranged adjacent to the comb spine portion 14, the space between the measurement electrodes 12a and 12b can be made more uniform, and more accurate measurement can be performed. Here, FIG. 2 is an enlarged plan view showing an enlarged part where a pair of measurement electrodes are arranged in another embodiment of the particulate matter detection device of the present invention (a particulate matter detection device 101).

It is to be noted that there is not any special restriction on a case where a comb spine covering portion 15 covers even tip portions of combteeth portions 13, but the comb spine covering portion preferably covers the tip portions of the combteeth portions 13 where widths of combteeth are not fixed in a combteeth extending direction. For example, when the combteeth of the combteeth portions 13 are formed to linearly extend and the tip portions thereof are rounded, a rounded portion of each tip portion is preferably covered. According to such a constitution, the electrode constituting a detecting portion is formed only by linear combteeth, and the satisfactory detection of a particulate matter can be performed.

Figure 3:
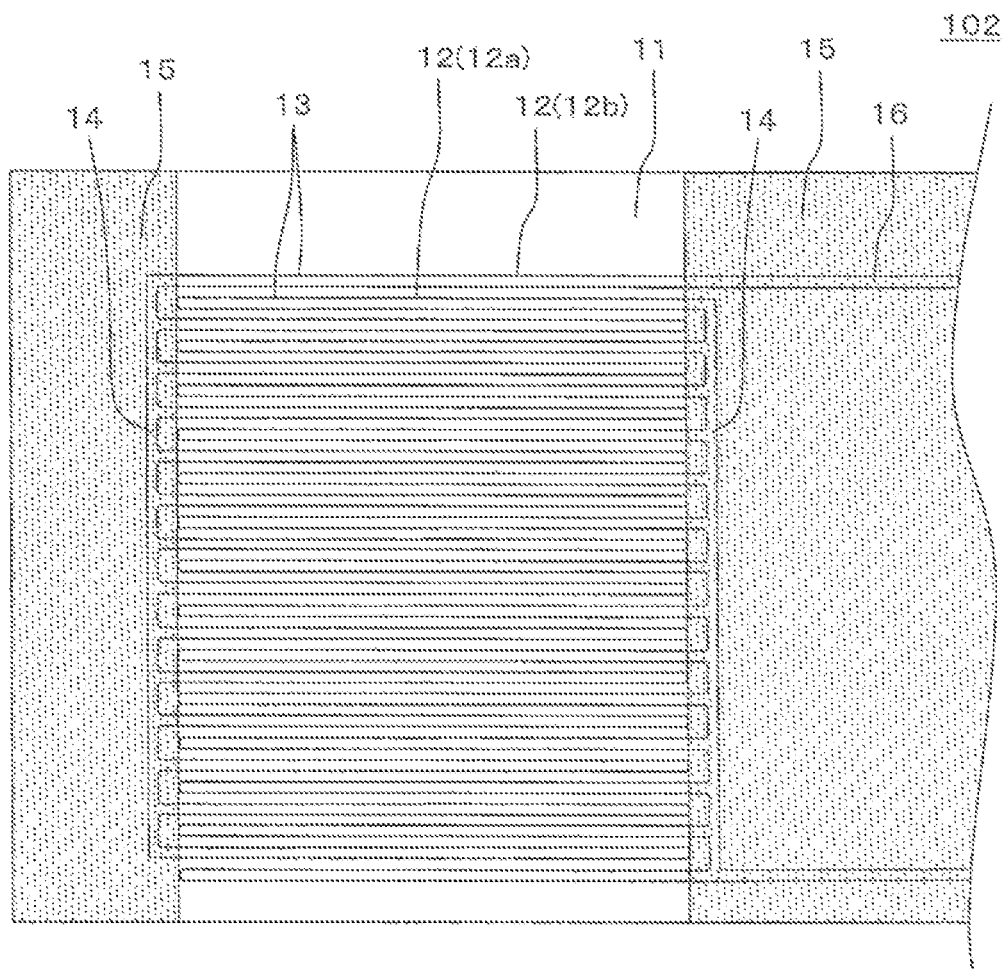
FIG. 3 is an enlarged plan view showing an enlarged part where a pair of measurement electrodes are arranged in still another embodiment of the particulate matter detection device of the present invention.

Moreover, for example, as shown in FIG. 3, a comb spine covering portion 15 may cover a comb spine portion 14 of one measurement electrode 12a so as to abut on tip portions of combteeth portions 13 of the other measurement electrode 12b arranged to engage with each other with a space being left therebetween. In FIG. 3, a comb spine portion 14 of the other measurement electrode 12b is also covered so as to abut on tip portions of combteeth portions 13 of the one measurement electrode 12a.

According to such a constitution, while enhancing a measurement sensitivity and a measurement accuracy, it is possible to enlarge a measurement surface. Here, FIG. 3 is an enlarged plan view showing an enlarged part where a pair of measurement electrodes are arranged in still another embodiment of the particulate matter detection device of the present invention (a particulate matter detection device 102).

Moreover, in the particulate matter detection devices 100, 101 and 102 shown in FIG. 1A to FIG. 3, the comb spine covering portions 15 which cover the comb spine portion 14 of the one measurement electrode 12a and the comb spine portion 14 of the other measurement electrode 12b are separately arranged. However, as shown in FIG. 4, a comb spine covering portion 15 may be disposed to cover the outer peripheries of combteeth electrodes so that the comb spine covering portion 15 covers a comb spine portion 14 of one measurement electrode 12a and a comb spine portion 14 of the other measurement electrode 12b in a particulate matter detection device 103.

Figure 4:
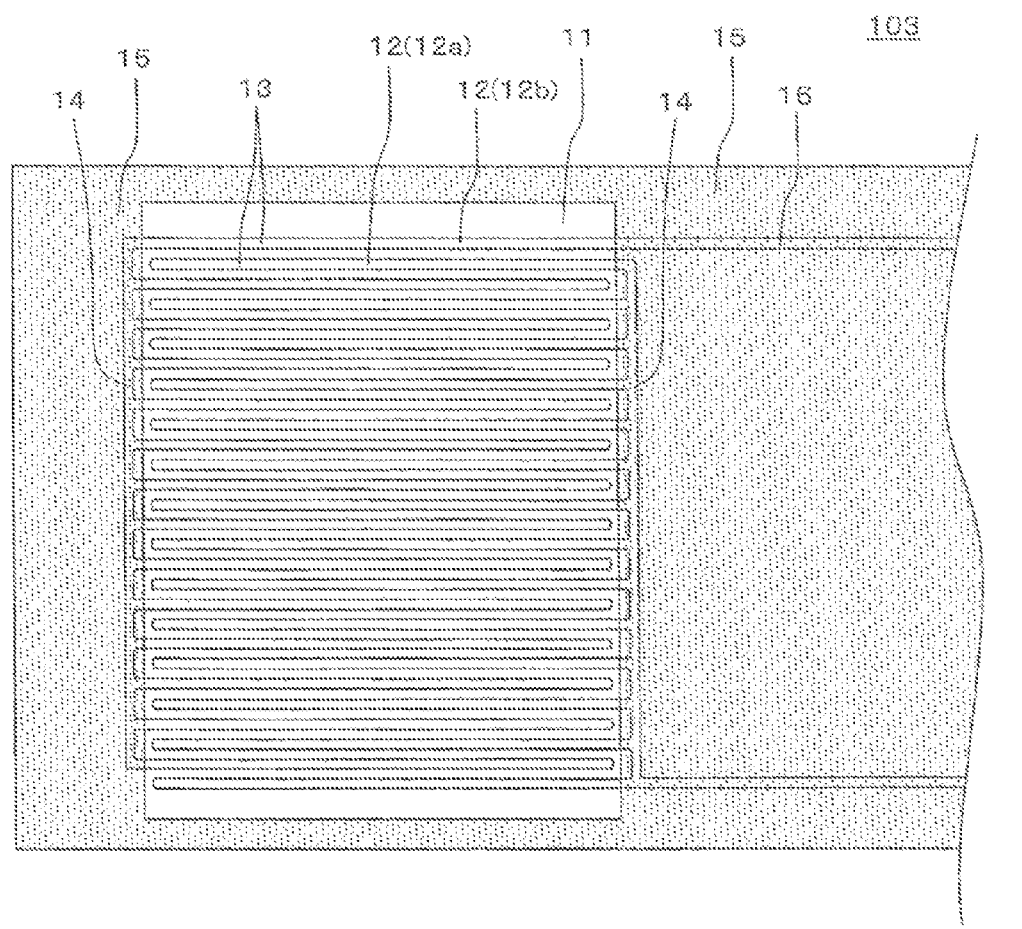
FIG. 4 is an enlarged plan view showing an enlarged part where a pair of measurement electrodes are arranged in a further embodiment of the particulate matter detection device of the present invention.

Here, FIG. 4 is an enlarged plan view showing an enlarged part where a pair of measurement electrodes are arranged in a further embodiment of the particulate matter detection device of the present invention (the particulate matter detection device 103). In consequence, there is not any special restriction on a shape of the comb spine covering portion in the particulate matter detection device of the present embodiment as long as combteeth portions are substantially exposed to the outside while covering the comb spine portions of the measurement electrodes.

It is to be noted that when a particulate matter is detected by the measurement electrodes 12a and 12b, the comb spine covering portions 15 made of a dielectric material are arranged so as to cover the comb spine portions 14 and spaces among the comb spine portions 14 and combteeth portions 13, whereby peripheries of the comb spine portions 14 do not contribute to the detection of the particulate matter (i.e., electric characteristics between the measurement electrodes 12a and 12b are not changed). Therefore, for example, a ratio (C3/C4) of "an electrostatic capacity C3 of the comb spine covering portion" with respect to "an electrostatic capacity C4 of a space in the upper surface of the comb spine covering portion" is preferably one digit or more smaller than a ratio (C1/C2) of "an electrostatic capacity C1 of an electrode protective film" with respect to "an electrostatic capacity C2 of a space in the upper surface of the electrode protective film". That is, a relation of "C1/C2"≥"C3/C4"×10 is preferably satisfied.

There is not any special restriction on a material of the comb spine covering portion made of the dielectric material, but the material is preferably at least one selected from the group consisting of, for example, alumina, cordierite, mullite, glass, zirconia, magnesia and titania. Among the materials, alumina can preferably be used. It is to be noted that this comb spine covering portion is preferably made of a material similar to an element base material in which the pair of measurement electrodes are arranged.

Moreover, the comb spine covering portion can be formed by using a ceramic green sheet obtained by forming the above ceramic material into a tape-like shape. For example, the ceramic green sheet is formed into such a shape as to cover the comb spine portions of the measurement electrodes, and this ceramic green sheet is disposed on the surfaces of the pair of measurement electrodes arranged to face each other, whereby the comb spine covering portion having a specific shape can be formed.

Figure 5A:
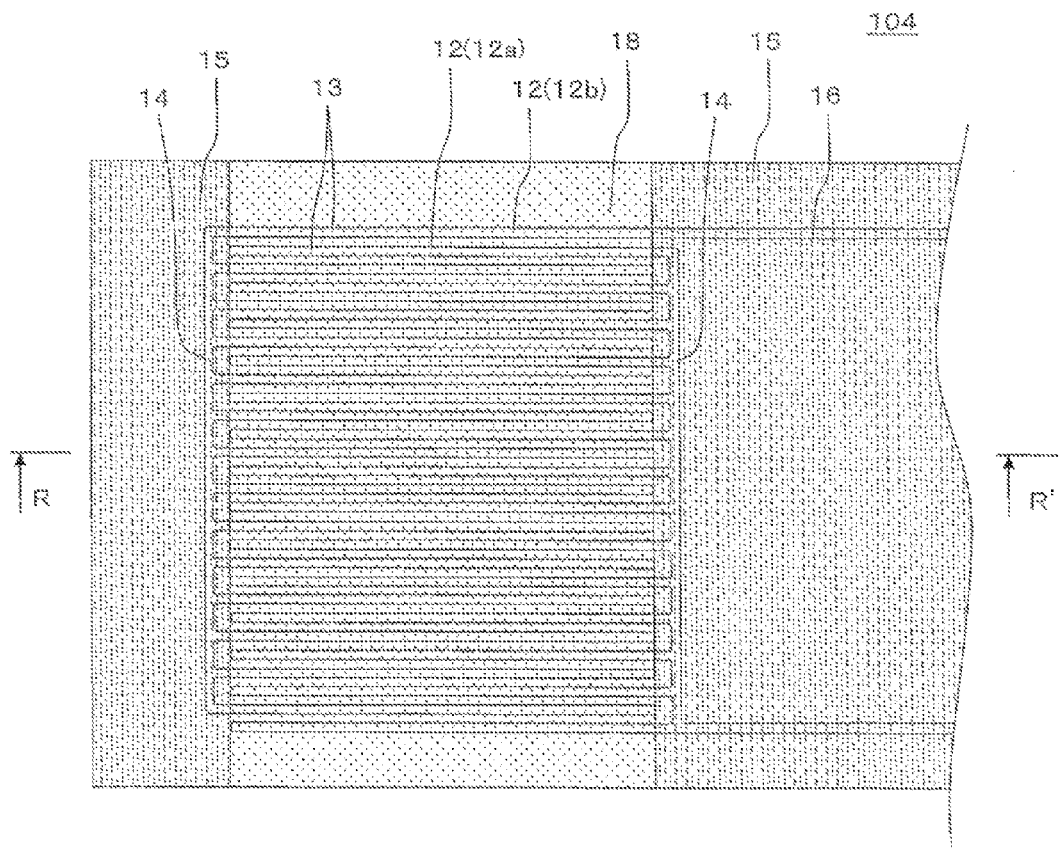
FIG. 5A is an enlarged plan view showing an enlarged part where a pair of measurement electrodes are arranged in a further embodiment of the particulate matter detection device of the present invention.
Figure 5B:
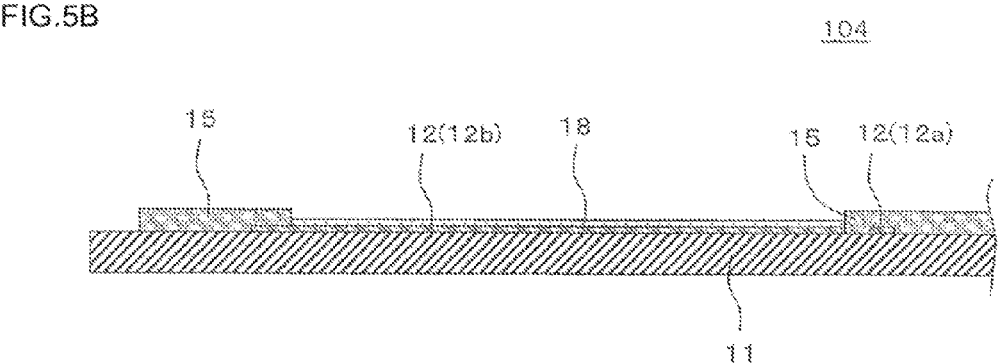
FIG. 5B is an exemplary diagram showing a section cut along the R-R' line of FIG. 5A.

Furthermore, in the particulate matter detection device of the present embodiment, for example, as shown in FIG. 5A and FIG. 5B, at least part of the surfaces of a pair of measurement electrodes 12a and 12b may be covered with an electrode protective film 18 which has a smaller thickness than a comb spine covering portion 15. Here, FIG. 5A is an enlarged plan view showing an enlarged part where a pair of measurement electrodes are arranged in a further embodiment of the particulate matter detection device of the present invention, and FIG. 5B is an exemplary diagram showing a section cut along the R-R' line of FIG. 5A. When such an electrode protective film covers the measurement electrodes, the corrosion of combteeth portions can be prevented. Moreover, while covering the combteeth portions having a function of a measurement surface with the above electrode protective film, comb spine portions are covered with comb spine covering portions having a larger thickness, whereby owing to the electrode protective film combined with the comb spine covering portions, the measurement of a particulate matter included in an exhaust gas can more satisfactorily be performed.

The electrode protective film 18 is a protective film having such a thickness that a change of electric characteristics measured between the pair of covered measurement electrodes 12a and 12b can be read, to protect the pair of measurement electrodes, when the particulate matter adheres to the surface of the film. There is not any special restriction on the thickness of the electrode protective film, but the thickness is, for example, preferably from 5 to 200 μm, further preferably from 10 to 100 μm, and especially preferably from 20 to 50 μm. For example, it is difficult to prepare a protective film having a thickness less than 5 μm, and a function of the protective film cannot sufficiently be performed. On the other hand, if the thickness exceeds 200 μm, the protective film is excessively thick, whereby a measurement sensitivity might lower owing to the protective film. It is to be noted that the thickness of the electrode protective film is preferably ⅕ or less of the thickness of the comb spine covering portion.

There is not any special restriction on a material of such an electrode protective film, but the film can be formed by using at least one selected from the group consisting of, for example, alumina, cordierite, mullite, glass, zirconia, magnesia and titania. It is to be noted that a pair of measurement electrodes are arranged in an element base material, whereby the element base material which covers the surfaces of the pair of measurement electrodes may form the above electrode protective film.

Moreover, as the particulate matter detection device described above, there has been illustrated an example where the pair of measurement electrodes are arranged on one surface of the element base material which is long in one direction, but the shape of the element base material is not limited to the above shape, as long as the pair of measurement electrodes are arranged on the surface of or in the element base material and the part where the pair of measurement electrodes are arranged is installed in the through channel of the measurement target gas to enable the detecting of the particulate matter.

For example, as shown in FIG. 6A to FIG. 6C and FIG. 7, the element base material may be a device main body 31 (the element base material) which includes at least a through hole (hollow) 32 formed in one end 31a thereof and which is long in one direction. When the device main body 31 is used, a pair of measurement electrodes 12a and 12b are arranged on the inner side surface of one wall which forms the through hole 32 or in the wall.

In a particulate matter detection device 105 shown in FIG. 6A to FIG. 6C and FIG. 7, a particulate matter included in a gas flowing into the through hole 32 is electrically adsorbed by the wall surface of the through hole 32, and by the pair of measurement electrodes 12a and 12b, a change of electric characteristics of the wall which forms the through hole 32 is measured, whereby it is possible to detect a mass of the particulate matter adsorbed by the wall surface of the through hole 32. In consequence, the particulate matter detection device 105 of the present embodiment allows the exhaust gas or the like to pass through the through hole 32, and can detect the particulate matter included in the exhaust gas.

The particulate matter detection device 105 does not directly measure all the particulate matter included in the exhaust gas flowing through a downstream side of a DPF or the like, but measures the particulate matter which has flowed into the through hole 32, whereby it is possible to roughly calculate the amount of the particulate matter of the whole exhaust gas on the basis of this measured value. In consequence, it is possible to measure a micro amount of the particulate matter, which cannot be detected by a conventional inspection method.

Moreover, the particulate matter detection device 105 does not measure the total amount of the exhaust gas as described above, and hence the particulate matter detection device 105 can be miniaturized and installed in a narrow space. Furthermore, with such miniaturization, the particulate matter detection device 105 can inexpensively be manufactured.

Moreover, when the total flow rate of the exhaust gas flowing through the downstream side of the DPF or the like is a high flow rate, only part of the exhaust gas (i.e., the particulate matter included in the exhaust gas) is introduced into the through hole 32. Therefore, the particulate matter in the through hole 32 can effectively be charged, and a measured value having less error can be obtained.

It is to be noted that as shown in FIG. 7 to FIG. 12, the particulate matter detection device 105 includes, in the wall which forms the through hole 32, at least a pair of dust collection electrodes 41 and 42 embedded outside a position where the pair of measurement electrodes 12a and 12b are embedded in the walls which form the through hole 32. When a voltage is applied to the dust collection electrodes 41 and 42, the particulate matter included in the gas flowing into the through hole 32 can electrically be adsorbed by the wall surface of the through hole 32.

Moreover, from the pair of measurement electrodes 12a and 12b, a pair of measurement wires 16a and 16b are extended toward the other end 31b of the device main body 31, and electrically connected to a pair of measurement lead terminals 17a and 17b. Moreover, the pair of dust collection electrodes 41 and 42 are electrically connected to dust collection lead terminals 41a and 42a via dust collection wires 41b and 42b. It is to be noted that the particulate matter detection device 105 shown in FIG. 6A to FIG. 12 is electrically connected to characteristics measurement means and particulate matter amount calculation means (not shown) from the above lead terminals via wires, to detect the particulate matter in accordance with the electric characteristics measured by the pair of measurement electrodes 12a and 12b.

Figure 6A:
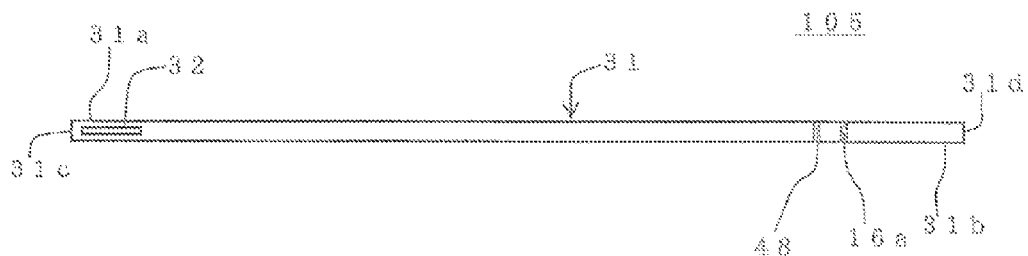
FIG. 6A is a front view schematically showing a still further embodiment of the particulate matter detection device of the present invention.
Figure 6B:
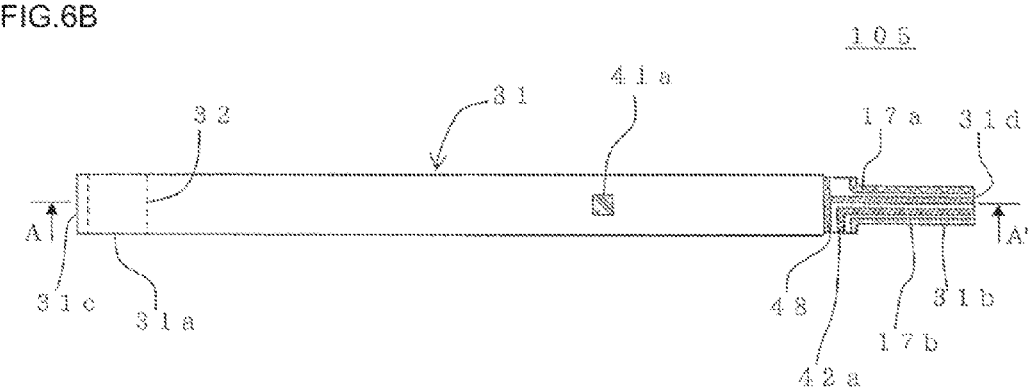
FIG. 6B is a side view showing one side surface of the particulate matter detection device shown in FIG. 6A.
Figure 6C:
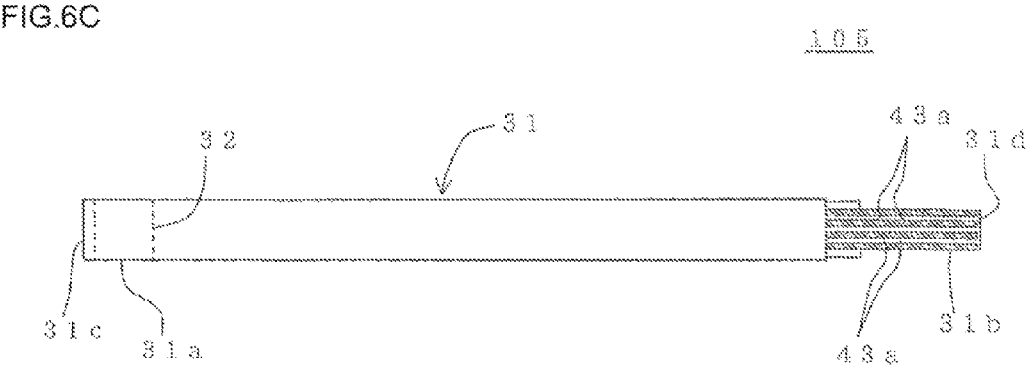
FIG. 6C is a side view showing the other side surface of the particulate matter detection device shown in FIG. 6A.
Figure 6D:
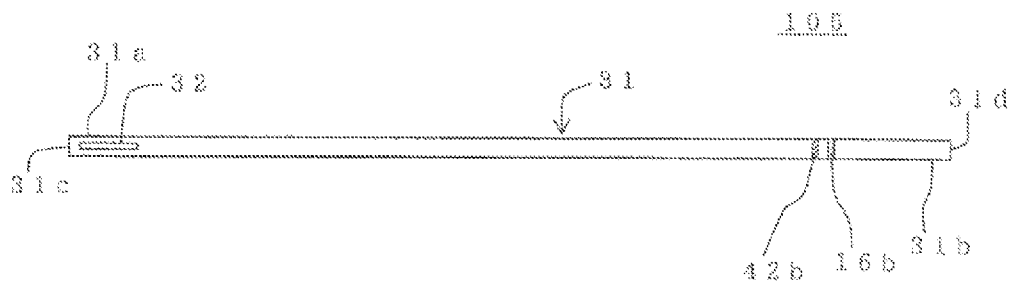
FIG. 6D is a back view of the particulate matter detection device shown in FIG. 6A.
Figure 7:
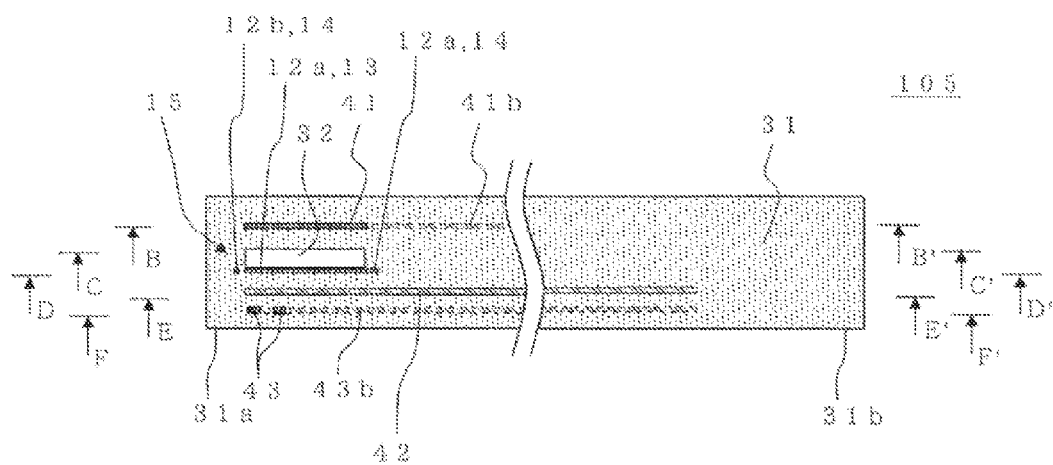
FIG. 7 is an exemplary diagram showing a section cut along the A-A' line of FIG. 6B.
Figure 8:
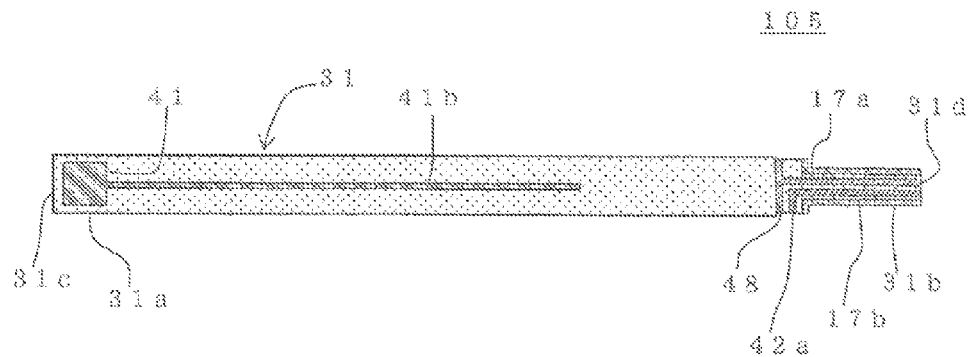
FIG. 8 is an exemplary diagram showing a section cut along the B-B' line of FIG. 7.
Figure 9:
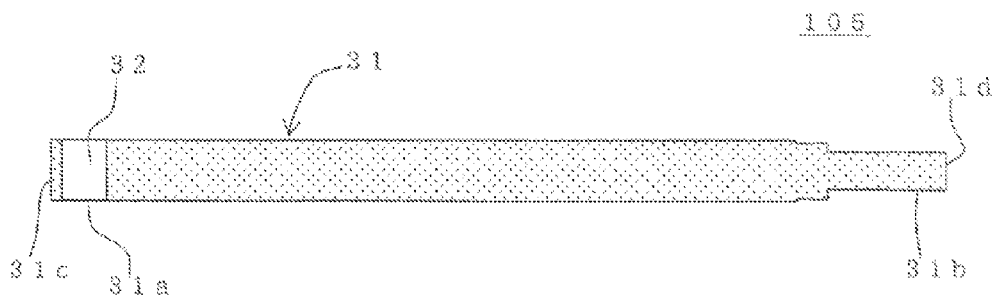
FIG. 9 is an exemplary diagram showing a section cut along the C-C' line of FIG. 7.
Figure 11:
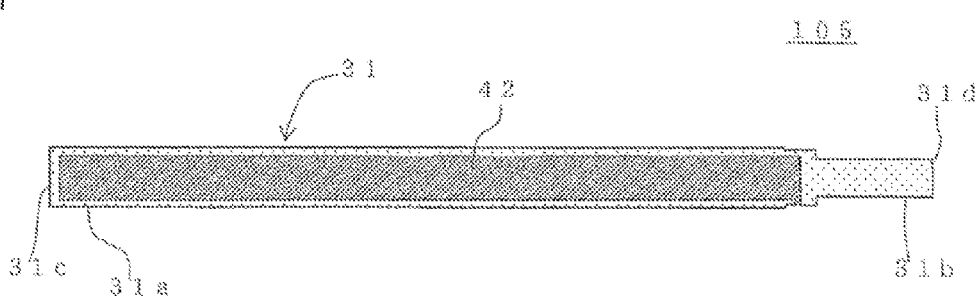
FIG. 11 is an exemplary diagram showing a section cut along the E-E' line of FIG. 7.
Figure 12:
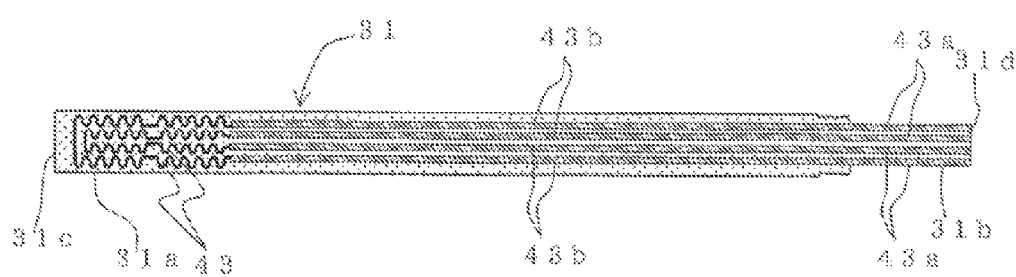
FIG. 12 is an exemplary diagram showing a section cut along the F-F' line of FIG. 7.

Here, FIG. 6A is a front view schematically showing a still further embodiment of the particulate matter detection device of the present invention, FIG. 6B is a side view showing one side surface of the particulate matter detection device shown in FIG. 6A, FIG. 6C is a side view showing the other side surface of the particulate matter detection device shown in FIG. 6A, and FIG. 6D is a back view of the particulate matter detection device shown in FIG. 6A. Moreover, FIG. 7 is an exemplary diagram showing a section cut along the A-A' line of FIG. 6B. Furthermore, FIG. 8 is an exemplary diagram showing a section cut along the B-B' line of FIG. 7, FIG. 9 is an exemplary diagram showing a section cut along the C-C' line of FIG. 7, FIG. 10 is an exemplary diagram showing a section cut along the D-D' line of FIG. 7, FIG. 11 is an exemplary diagram showing a section cut along the E-E' line of FIG. 7, and FIG. 12 is an exemplary diagram showing a section cut along the F-F' line of FIG. 7.

Figure 10:
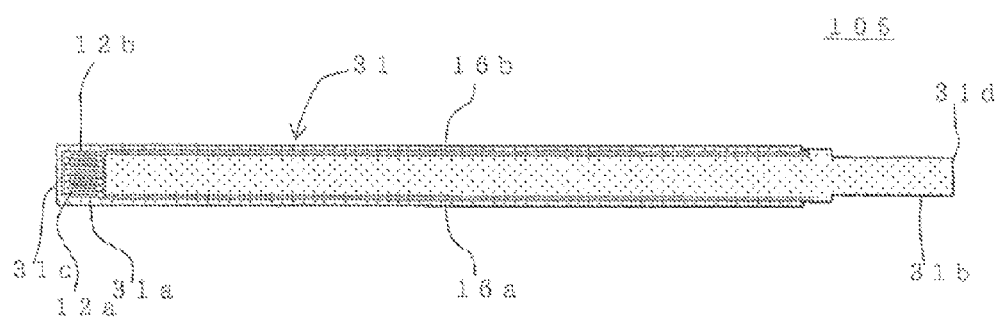
FIG. 10 is an exemplary diagram showing a section cut along the D-D' line of FIG. 7.

As shown in FIG. 7 and FIG. 10, in the particulate matter detection device 105 of the present embodiment, the pair of measurement electrodes 12a and 12b are preferably arranged so that a direction in which combteeth of combteeth portions 13 of the measurement electrodes 12a and 12b extend is orthogonal to a direction in which the through hole 32 extends through the device. In this case, the combteeth portions 13 of the pair of measurement electrodes 12a and 12b are arranged so that a wall portion of the through hole 32 becomes a comb spine covering portion in the present invention (a comb spine covering portion 15 in FIG. 7) in accordance with a length of the through hole 32 in a longitudinal direction of a device main body 31 in FIG. 6A. Comb spine portions 14 of the respective measurement electrodes are preferably arranged in a wall extending vertically from the wall provided with the pair of measurement electrodes 12a and 12b, among the walls which form the through hole 32. When part of the walls which form the through hole 32 is used as the comb spine covering portion 15 in this manner, it is not necessary to separately dispose a member for covering the comb spine portion 14, and it is possible to obtain the particulate matter detection device which more easily satisfies the constitution of the present invention.

Hereinafter, the particulate matter detection device 105 shown in FIG. 6A to FIG. 12 will be described as an example of the particulate matter detection device of the present embodiment in more detail.

[2] Constitution of Particulate Matter Detection Device:

A particulate matter detection device 105 shown in FIG. 6A to FIG. 6D and FIG. 7 to FIG. 12 includes a device main body 31 (an element base material) which includes at least one through hole (hollow) 32 formed in one end 31a and which is long in one direction; at least a pair of measurement electrodes 12a and 12b arranged on the inner side surface of one wall which forms the through hole 32 or in the wall; and at least a pair of dust collection electrodes 41 and 42 embedded in walls which form the through hole 32 and which face each other, embedded outside a position where the pair of measurement electrodes 12a and 12b are embedded in the walls which form the through hole 32, and covered with a dielectric material, to detect a particulate matter included in an exhaust gas by the particulate matter detection device 105. It is to be noted that when an electric field is generated in the through hole by the above dust collection electrodes, the particulate matter included in the gas passing through the through hole can be adsorbed by the wall surfaces of the walls which form the through hole. Moreover, the particulate matter detection device 105 further includes a heating portion 43 for burning and removing the particulate matter adhering to the device.

[2-1] Device Main Body (Element Base Material):

The device main body is a part which includes at least one through hole formed in one end and which is long in one direction to become a base body of a particulate matter detection device. The device main body is made of a dielectric material, and in walls which form this through hole and which face each other, at least a pair of dust collection electrodes are arranged, respectively. When a voltage is applied to this pair of dust collection electrodes, an electric field can be generated in the through hole. Moreover, in this particulate matter detection device, part of the walls which form the through hole also serves as a comb spine covering portion for covering comb spine portions of a pair of measurement electrodes.

The dielectric material constituting the device main body is preferably at least one selected from the group consisting of, for example, alumina, cordierite, mullite, glass, zirconia, magnesia and titania. Among the materials, alumina can preferably be used. When the dust collection electrodes are embedded in the device main body made of such a dielectric material, the dust collection electrodes covered with the dielectric material can be formed. Therefore, the particulate matter detection device has an excellent thermal resistance, dielectric breakdown resisting properties and the like. Here, "the dielectric material" is a substance which is excellent in dielectric properties rather than in conductivity and which behaves as an insulator against a direct-current voltage.

It is to be noted that "the one end of the device main body" is a region from one tip portion 31c of the device main body to a position corresponding to a length which is 50% of the total length of the device main body 31. Moreover, "the other end of the device main body" is a region from the other tip portion 31d of the device main body to a position corresponding to a length which is 50% of the total length of the device main body 31. It is to be noted that the one end of the device main body is preferably a region from the one tip portion 31c of the device main body to a position corresponding to a length which is preferably 40%, and further preferably 30% of the total length of the device main body 31. Moreover, the other end of the device main body is a region from the other tip portion 31d of the device main body to a position corresponding to a length which is preferably 40%, and further preferably 30% of the total length of the device main body 31. A position between the one end 31a and the other end 31b of the device main body 31 is a portion obtained by excluding the above regions of the one end 31a and the other end 31b from the device main body 31 (see FIG. 6A to FIG. 6D).

In the particulate matter detection device 105 shown in FIG. 6A to FIG. 6D, the device main body 31 is formed to be long in one direction, and there is not any special restriction on the length of the body in a longitudinal direction thereof, but the device main body preferably has such a length that the particulate matter in the exhaust gas can efficiently be sampled when the main body is inserted into an exhaust gas pipe.

Moreover, there is not any special restriction on a thickness of the device main body 31 (a length thereof in a direction (a thickness direction) which is vertical both to "the longitudinal direction of the device main body" and "a gas circulating direction"), but the length is, for example, preferably from about 0.5 to 3 mm. Here, "the thickness of the device main body 31" is the thickness of the thickest portion of the device main body in the above thickness direction. Moreover, there is not any special restriction on the length of the device main body 31 in the circulating direction when the gas circulates through the through hole 32 (the length of the device main body in the gas circulating direction), but the length is, for example, preferably from about 2 to 20 mm. Furthermore, the length of the device main body 31 in the longitudinal direction is preferably from 10 to 100 times as much as the thickness of the device main body 31, and preferably from 3 to 10 times as much as the length of the device main body 31 in the gas circulating direction.

As to a shape of the device main body 31, as shown in FIG. 6A to FIG. 6D, a sectional shape which is orthogonal to the longitudinal direction may be a rectangular plate-like shape, or the sectional shape may be a round rod-like shape, an elliptic rod-like shape or the like (not shown). Moreover, the device main body may have another shape as long as the shape is long in one direction.

In the particulate matter detection device 105, there is not any special restriction on a shape and a size of the through hole 32, as long as the exhaust gas is allowed to pass through the through hole and the amount of the particulate matter can be measured. However, in the particulate matter detection device 105 of the present embodiment, part of the walls which form the through hole 32 can be "the comb spine covering portion 15". For this purpose, the comb spine portions 14 of the pair of measurement electrodes 12a and 12b are preferably formed into such a size that the comb spine portions are hidden behind (covered with) the walls which form the through hole 32 (specifically, the wall extending vertically from the wall provided with the above pair of measurement electrodes, among the walls which form the through hole). For example, a length of the through hole 32 in the longitudinal direction of the detection device main body is preferably from about 2 to 20 mm. Moreover, a width of a portion of the through hole 32 sandwiched between the dust collection electrodes 41 and 42 (the length of the through hole in the direction which are vertical both to the longitudinal direction of the detection device main body and the gas circulating direction) is preferably from about 3 to 30 mm.

It is to be noted that when the size of the through hole 32 is set to the above range, the exhaust gas including the particulate matter can sufficiently be circulated through the through hole 32, and further by the electric field generated by the dust collection electrodes 41 and 42, the particulate matter can effectively be adsorbed in the through hole 32.

The device main body 31 is preferably obtained by laminating a plurality of tape-like ceramic materials (ceramic sheets). In consequence, the particulate matter detection device can be prepared by laminating the plurality of tape-like ceramic materials while sandwiching electrodes, wires and the like among the materials, whereby the particulate matter detection device can efficiently be manufactured.

[2-2] Measurement Electrode:

At least a pair of measurement electrodes are arranged on the inner side surface of one wall which forms a through hole or in the wall, to detect a particulate matter included in an exhaust gas passing through an exhaust gas system, on the basis of a change of electric characteristics of the wall which forms the through hole, generated when the particulate matter is electrically adsorbed by the wall surface of the through hole through dust collection electrodes.

A pair of measurement electrodes 12a and 12b for use in a particulate matter detection device 105 of the present embodiment are combteeth-like electrodes each including a plurality of planarly arranged combteeth portions 13, and a comb spine portion 14 which connects the plurality of combteeth portions 13 of the measurement electrode 12a or 12b to one another at one end of each of the plurality of combteeth portions, and the combteeth portions 13 of the measurement electrodes 12a and 12b are arranged to engage with each other with a space being left therebetween.

There is not any special restriction on a thickness of the measurement electrode (the combteeth portions 13 and the comb spine portion 14), but the thickness is, for example, preferably from 5 to 30 μm. Moreover, examples of a material of the measurement electrode include platinum (Pt), molybdenum (Mo) and tungsten (W).

There is not any special restriction on a width of each of the combteeth portions constituting the measurement electrode, but the width is, for example, preferably from 30 to 400 μm, further preferably from 50 to 300 μm, and especially preferably from 80 to 250 μm. Moreover, there is not any special restriction on the number of the combteeth portions arranged in each measurement electrode, but the number is, for example, preferably at least 3 or more, further preferably from 3 to 20, and especially preferably from 4 to 8. According to such a constitution, the particulate matter can more accurately be detected.

A space between the combteeth portion of one of adjacent measurement electrodes and the combteeth portion of the other measurement electrode (i.e., a space where the combteeth portions are arranged to engage with each other) is, for example, preferably from 30 to 400 μm, further preferably from 50 to 300 μm, and especially preferably from 80 to 250 μm. A space between the combteeth portion and the comb spine portion is usually larger than the above numeric value range, and owing to this space between the combteeth portion and the comb spine portion, a measurement accuracy of the device might lower. In the particulate matter detection device of the present embodiment, however, the comb spine portion is covered with a comb spine covering portion (i.e., the wall which forms the through hole). Therefore, the space between the electrodes in the measurement surface of the detection device becomes uniform, which can enhance a measurement accuracy.

Moreover, the pair of measurement electrodes 12a and 12b of the particulate matter detection device 105 include measurement lead terminals 17a and 17b (hereinafter referred to simply as "the lead terminals 17a and 17b" sometimes) in the other end 31b of a device main body 31 via a measurement wire 16. The measurement lead terminals 17a and 17b are electrically connected to characteristics measurement means 20 and particulate matter amount calculation means 21 (see FIG. 1A), and the particulate matter is detected on the basis of a change of electric characteristics measured by the pair of measurement electrodes 12a and 12b.

It is to be noted that when the lead terminals 17a and 17b of the pair of measurement electrodes 12a and 12b are arranged in the other end 31b of the device main body 31 in this manner, it is possible to obtain large spaces among a portion provided with a through hole 32 (i.e., one end 31a) and the lead terminals 17a and 17b. Therefore, the only one end 31a provided with the through hole 32 and the like is inserted into a pipe through which a high-temperature exhaust gas circulates, and the other end 31b side provided with the lead terminals 17a and 17b can be extended outwardly from the pipe. When temperatures of the lead terminals 17a and 17b are set to be high, a detection accuracy of the particulate matter lowers, and it becomes difficult to perform stable detection. When the terminals are used for a long period of time, a contact defect among electric terminals and a harness connected to the outside is generated, and measurement might not be performed. The lead terminals 17a and 17b are extended outwardly from the pipe, and are not exposed to the high temperature, whereby the particulate matter can accurately and stably be detected.

As shown in FIG. 6B, the lead terminals 17a and 17b arranged in the other end 31b of the device main body 31 are preferably arranged on the side surface of the other end 31b of the device main body 31, to extend in a longitudinal direction. It is to be noted that in FIG. 6B, a width of the other end 31b of the device main body 31 becomes narrow, but the width of the other end 31b may be narrowed in this manner or does not have to be narrowed. There is not any special restriction on a shape and a size of the lead terminals 17a and 17b, but each lead terminal preferably has a strip-like shape with a width from 0.1 to 2.0 mm and a length from 0.5 to 20 mm. Examples of a material of the lead terminals 17a and 17b include nickel (Ni), platinum (Pt), chromium (Cr), tungsten (W), molybdenum (Mo), aluminum (Al), gold (Au), silver (Ag) and copper (Cu).

[2-3] Dust Collection Electrode:

Dust collection electrodes are embedded in walls which form a through hole and which face each other, embedded outside a position where the above pair of measurement electrodes are embedded in the walls which form the through hole, and covered with a dielectric material constituting a device main body. When a predetermined voltage is applied across dust collection electrodes 41 and 42, an electric field can be generated in the through hole 32.

There is not any special restriction on a shape of the dust collection electrodes, as long as the electrodes are embedded in the walls which form the through hole and an electric field can be generated in the through hole 32. In the particulate matter detection device 105 of the present embodiment, as shown in FIG. 8, one of the dust collection electrodes is the high-voltage dust collection electrode 41 disposed in a wall in which a pair of measurement electrodes 12a and 12b are arranged and in a wall on an opposite side from the through hole 32 (see FIG. 7), and a high voltage is applied to the electrode. Moreover, as shown in FIG. 11, the other dust collection electrode is the grounded ground dust collection electrode 42 disposed in the wall on the same side as the wall in which the pair of measurement electrodes 12a and 12b are arranged (see FIG. 7). There is not any special restriction on a thickness of each dust collection electrode, but the thickness is, for example, preferably from 5 to 30 μm. Moreover, examples of a material of the dust collection electrode include platinum (Pt), molybdenum (Mo), and tungsten (W).

There is not any special restriction on a shape and a size of the dust collection electrodes 41 and 42, as long as the electric field can be generated in the through hole 32. Examples of the shape include a rectangular shape, a round shape, and an oblong shape. Moreover, as to the size of the dust collection electrodes 41 and 42, an area thereof is, for example, preferably 70% or more of that of the through hole 32 as seen from the side surface.

For example, FIG. 8 shows an example where the high-voltage dust collection electrode 41 is formed in almost the same size as the through hole. The high-voltage dust collection electrode 41 is connected to a dust collection wire 41b (hereinafter referred to simply as "the wire" sometimes) extending in a longitudinal direction of a device main body 31, and a tip portion (a tip on a side which is not connected to the electrode 41) of the wire 41b is interlayer-connected (via-connected) to a dust collection lead terminal 41a (hereinafter referred to simply as "the lead terminal" sometimes) shown in FIG. 6B. There is not any special restriction on a width of the wire 41b, but the width is, for example, preferably from about 0.2 to 1 mm. Moreover, there is not any special restriction on a thickness of the wire 41b, but the thickness is, for example, preferably from about 5 to 30 μm. Furthermore, examples of a material of the wire 41b include platinum (Pt), molybdenum (Mo), and tungsten (W).

It is to be noted that both lead terminals of the pair of dust collection electrodes may be arranged in the other end of the device main body. As shown in FIG. 6A to FIG. 6D, however, a lead terminal 42a (a dust collection lead terminal) of the grounded dust collection electrode (the ground dust collection electrode 42) is preferably disposed in the other end 31b of the device main body 31, and the lead terminal 41a of the high-voltage dust collection electrode 41 is preferably disposed at a position between the one end 31a and the other end 31b of the device main body 31. In consequence, the lead terminal 42a of the ground dust collection electrode 42 and the lead terminal 41a of the high-voltage dust collection electrode 41 can be arranged with a space being left therebetween. Therefore, when a voltage is applied between the lead terminal 41a and the lead terminal 42a to apply the voltage between the pair of dust collection electrodes 41 and 42, surface discharge can effectively be prevented from occurring on the surface of the device main body 31.

In the particulate matter detection device 105, a distance between the lead terminal 41a and the lead terminal 42a is preferably from 5 to 100 mm, and further preferably from 10 to 70 mm. If the distance is smaller than 5 mm, short-circuit due to the surface discharge might easily occur. On the other hand, if the distance is larger than 100 mm and the device main body 31 of the particulate matter detection device 105 is attached to a pipe or the like so that the lead terminal 41a is positioned outside the pipe, a portion of the device main body 31 projecting outwardly from the pipe becomes excessively long, and it might become difficult to attach the device main body 31 to a narrow space.

Moreover, a distance from the lead terminal 41a disposed at the position between the one end 31a and the other end 31b of the device main body 31 to the through hole 32 is preferably 10 mm or more, and further preferably 20 mm or more. If the distance is smaller than 10 mm and the particulate matter detection device 105 is attached to the pipe so as to insert the portion of the through hole 32 into the pipe, heat of a high-temperature exhaust gas circulating through the pipe might easily affect the lead terminal 41a.

There is not any special restriction on a shape and a size of the lead terminal 41a of the high-voltage dust collection electrode 41. The lead terminal preferably has a polygonal shape such as a quadrangular shape having a width of 0.5 to 3 mm and a length of 0.5 to 3 mm, but the shape may be another shape such as a round shape, an elliptic shape or a race track shape. Examples of a material of the lead terminal 41a include nickel (Ni), platinum (Pt), chromium (Cr), tungsten (W), molybdenum (Mo), aluminum (Al), gold (Au), silver (Ag), copper (Cu), stainless steel, and Kovar.

A distance between the high-voltage dust collection electrode 41 and the through hole 32 and a distance between the ground dust collection electrode 42 and the through hole 32 are preferably from 50 to 500 μm, and further preferably from 100 to 300 μm. In such a range, the electric field can effectively be generated in the through hole. The distance between the dust collection electrode 41 or 42 and the through hole 32 is a thickness of a portion of a dielectric material covering each dust collection electrode 41 or 42 which faces the through hole 32.

Conditions of the electric field generated by the dust collection electrodes vary in accordance with a gap (a distance between the pair of dust collection electrodes), or a gas temperature, but are preferably from 50 to 200 kV/cm.

The particulate matter detection device 105 allows the particulate matter included in a fluid (i.e., the exhaust gas) flowing into the through hole 32 to be electrically adsorbed by the wall surface of the through hole 32, and reads a change of electric characteristics due to the adsorption of the particulate matter to detect the particulate matter included in the exhaust gas. When the particulate matter in the exhaust gas is already charged before flowing into the through hole 32, the particulate matter is adsorbed by the electric field generated in the through hole 32. On the other hand, if the particulate matter is not charged, the particulate matter is charged with the electric field generated in the through hole 32, and the charged particulate matter is electrically adsorbed by the wall surface of the through hole 32.

[2-4] Characteristics Measurement Means and Particulate Matter Amount Calculation Means:

Characteristics measurement means and particulate matter amount calculation means are used to detect electric characteristics between a pair of measurement electrodes. Specifically, when the electric characteristics to be measured are, for example, an electrostatic capacity, an LCR meter 4263B manufactured by Agilent Technologies Inc. or the like can be used. It is to be noted that as the characteristics measurement means and the particulate matter amount calculation means, it is possible to use means for use in a heretofore known particulate matter detection device which measures electric characteristics between a pair of electrodes to detect a particulate matter.

A particulate matter detection device 105 shown in FIG. 6A to FIG. 6D has a constitution in which lead terminals of measurement electrodes 12a and 12b are electrically connected to characteristics measurement means 20 and particulate matter amount calculation means 21 (see FIG. 1A), whereby electric characteristics of the measurement electrodes 12a and 12b can be detected.

[2-5] Heating Portion:

A particulate matter detection device 105 shown in FIG. 7 and FIG. 12 includes a heating portion 43 which is disposed (embedded) in a device main body 31 so as to extend along a wall surface of a through hole 32 (the wall surface which is parallel to the side surface of the device main body 31). When the device is heated by the heating portion 43, a particulate matter adsorbed by walls forming the through hole 32 can be heated and oxidized (i.e., the device can be regenerated). Moreover, during measurement of a mass of the particulate matter or the like, an internal space of the through hole 32 is adjusted at a desirable temperature, and the temperature can be regulated so as to stably measure a change of electric characteristics of the walls which form the through hole 32.

The heating portion 43 may have a wide film-like shape, but as shown in FIG. 12, a linear metal material may be disposed in a wave-like shape so that a tip portion thereof is U-turned. According to such a shape, the inside of the through hole can uniformly be heated, and the particulate matter adhering to the device main body 31 or a pair of measurement electrodes 12a and 12b can be removed.

Examples of a material of the heating portion 43 include platinum (Pt), molybdenum (Mo), and tungsten (W). The heating portion 43 is preferably embedded in the device main body 31 so as to extend along the wall surface of the through hole 32, but as shown in FIG. 12, the heating portion may be formed to extend along a position provided with the through hole 32 and also to the other end 31b side of the device main body 31. In consequence, there are advantages that a temperature difference between the inside of the through hole and the periphery of the through hole can be decreased. Even if rapid heating is performed, the breakdown of the element (the detection device main body) advantageously does not easily occur. The heating portion can preferably raise the temperature of the internal space of the through hole up to 650° C.

Moreover, FIG. 12 illustrates an example where two heating portions 43 are formed by two wires, but one heating portion may be disposed, or three or more heating portions may be arranged. Furthermore, although not shown, the heating portions may be arranged on both side walls which form the through hole. That is, the arrangement and number of the heating portions can be set to those required for achieving objects such as the oxidizing and removing of the collected particulate matter or temperature adjustment.

Furthermore, the heating portions 43 shown in FIG. 12 are connected to heating wires 43b (hereinafter referred to simply as "the wires 43b" sometimes), and the wires 43b are interlayer-connected to lead terminals 43a (heating lead terminals), respectively, as shown in FIG. 12. The lead terminals 43a of the heating portions 43 are preferably arranged in the other end 31b of the device main body 31 in the same manner as in the lead terminals 17a and 17b of the measurement electrodes 12a and 12b, to avoid the influence of the heat when the one end 31a side of the device main body 31 is heated. In FIG. 12, four lead terminals 43a are arranged side by side in the other side surface of the device main body 31, but the arrangement of the lead terminals 43a is not limited to such arrangement.

[3] Manufacturing Method of Particulate Matter Detection Device:

Next, a method of manufacturing the particulate matter detection device 105 shown in FIG. 6A to FIG. 6D will be described as an example of a manufacturing method of the particulate matter detection device of the present embodiment. It is to be noted that the method of manufacturing the particulate matter detection device of the present invention is not limited to the following manufacturing method.

[3-1] Preparation of Forming Raw Material:

First, a forming raw material for manufacturing the device main body 31 (the element base material) is prepared. Specifically, at least one ceramic raw material (a dielectric raw material) selected from the group consisting of, for example, alumina, a cordierite forming material, mullite, glass, zirconia, magnesia and titania is mixed with another component for use as the forming raw material, to prepare a slurried forming raw material. As the ceramic raw material (the dielectric raw material), the above raw material is preferable, but the raw material is not limited to the above example. As another raw material, a binder, a plasticizer, a dispersant, a dispersion medium or the like is preferably used.

There is not any special restriction on a binder, but an aqueous binder or a nonaqueous binder may be used. As the aqueous binder, methyl cellulose, polyvinyl alcohol, polyethylene oxide or the like can preferably be used, and as the nonaqueous binder, polyvinyl butyral, acrylic resin, polyethylene, polypropylene or the like can preferably be used.

Examples of the acrylic resin include (meth)acrylic resin, (meth)acrylic ester copolymer, and acrylic ester-methacrylic ester copolymer.

An amount of the binder to be added is preferably from 3 to 20 parts by mass, and further preferably from 6 to 17 parts by mass with respect to 100 parts by mass of the dielectric raw material. With such a binder content, when the slurried forming raw material is formed into a green sheet, dried and fired, the generation of cracks or the like can be prevented.

As the plasticizer, glycerin, polyethylene glycol, dibutyl phthalate, di-2-ethyl hexyl phthalate, diisononyl phthalate or the like can be used.

An amount of the plasticizer to be added is preferably from 30 to 70 parts by mass, and further preferably from 45 to 55 parts by mass with respect to 100 parts by mass of the binder. If the amount is larger than 70 parts by mass, the green sheet becomes excessively soft, and is easily deformed in a step of processing the sheet. If the amount is smaller than 30 parts by mass, the green sheet becomes excessively hard. In this case, when the green sheet is simply bent, the green sheet is cracked, which might deteriorate handling properties.

As an aqueous dispersant, anionic surfactant, wax emulsion, pyridine or the like can be used, and as a nonaqueous dispersant, fatty acid, phosphate ester, synthetic surfactant or the like can be used.

An amount of the dispersant to be added is preferably from 0.5 to 3 parts by mass, and further preferably from 1 to 2 parts by mass with respect to 100 parts by mass of the dielectric raw material. If the amount is smaller than 0.5 part by mass, dispersibility of the dielectric raw material might lower, and cracks or the like might be generated in the green sheet. If the amount is larger than 3 parts by mass, the dispersibility of the dielectric raw material does not change, but impurities during firing increase.

As the dispersion medium, water can be used. An amount of the dispersion medium to be added is preferably from 50 to 200 parts by mass, and further preferably from 75 to 150 parts by mass with respect to 100 parts by mass of the dielectric raw material.

The above raw materials are sufficiently mixed by use of a pot made of alumina and an alumina ball, to prepare a slurried forming raw material for preparing the green sheet. Moreover, these materials are mixed in a ball mill by use of a mono ball, whereby the forming raw material may be prepared.

Next, the obtained slurried forming raw material for preparing the green sheet is stirred and defoamed under a reduced pressure, and further prepared to obtain a predetermined viscosity. The viscosity of the slurried forming raw material obtained in the preparation of the forming raw material is preferably from 2.0 to 6.0 Pa·s, further preferably from 3.0 to 5.0 Pa·s, and especially preferably from 3.5 to 4.5 Pa·s. When a viscosity range is regulated in this manner, the slurry is preferably easily formed into a sheet-like shape. If the slurry viscosity is excessively high or low, it might become difficult to form the sheet. It is to be noted that the viscosity of the slurry is a value measured with a B-type viscosity meter.

[3-2] Forming Processing:

Next, the slurried forming raw material obtained by the above method is formed and processed into a tape-like shape, to prepare a green sheet which is long in one direction. There is not any special restriction on a forming/processing process, as long as the forming raw material can be formed into the sheet-like shape to form the green sheet, and a known process such as a doctor blade process, a press forming process, a rolling process and a calendar rolling process can be used. At this time, a green sheet for forming a through hole is prepared so as to form the through hole when green sheets are laminated. A thickness of the green sheet to be prepared is preferably from 50 to 800 μm.

On the surface of the obtained green sheet, electrodes (a pair of measurement electrodes and dust collection electrodes), wires, heating portions and lead terminals are arranged. When the particulate matter detection device 105 shown in FIG. 6A to FIG. 6D is prepared, as shown in FIG. 8 to FIG. 12, the electrodes, the wires, the heating portions and the lead terminals are preferably printed at corresponding positions of the green sheet so as to arrange the electrodes, the wires, the heating portions and the lead terminals at the predetermined positions. In particular, sizes of combteeth portions and comb spine portions and a size of the through hole are preferably determined so that a comb spine portion of each combteeth-like measurement electrode is hidden behind (covered with) walls which form the through hole of the device main body.

As to a conductive paste for forming (printing) the electrodes, the wires, the heating portions and the lead terminals, in accordance with materials required for forming the electrodes, the wires and the like, a binder and a solvent such as terpineol are added to powder containing at least one selected from the group consisting of gold, silver, platinum, nickel, molybdenum, and tungsten, and sufficiently kneaded by using a tri-roll mill or the like, whereby the paste can be prepared. The conductive paste formed in this manner and containing the materials required for forming the electrodes, the wires and the like is printed on the surface of the green sheet by use of screen printing or the like, to prepare the electrodes, the wires, the heating portions and the lead terminals having predetermined shapes.

Further specifically, a plurality of green sheets are prepared, and on one surface of each of two green sheets among the plurality of green sheets, dust collection electrodes are arranged. If necessary, wires are arranged on the arranged dust collection electrodes, respectively, to prepare two green sheets provided with the dust collection electrodes.

Furthermore, at a position of another green sheet where the through hole of the device main body is to be formed, combteeth portions of the pair of measurement electrodes are arranged, to form the green sheet provided with the measurement electrodes. It is to be noted that in this case, there are arranged a pair of measurement wires extending from the measurement electrodes to the other end of the detection device main body, respectively.

Furthermore, at positions superimposed on the combteeth portions of the measurement electrodes when superimposed on the green sheet provided with the measurement electrodes, such a cut portion as to form the through hole is formed to prepare the green sheet provided with the cut portion.

Furthermore, at a position of still another green sheet where at least the through hole is to be formed, the heating portions are arranged to form the green sheet provided with the heating portions. On this green sheet provided with the heating portions, there are also arranged wires extending toward the other end of the device main body.

Afterward, on the two green sheets provided with the dust collection electrodes, respectively, another green sheet which is not provided with electrodes or the like is superimposed to obtain a state where the dust collection electrodes and the wires are covered with the green sheet, thereby forming the green sheet including the embedded dust collection electrodes. Then, the green sheets are laminated so that the green sheet provided with the measurement electrodes and the green sheet provided with the cut portion are sandwiched between the two green sheets including the embedded dust collection electrodes. Furthermore, the green sheet provided with the heating portions is laminated on the outside of the above green sheet, to form a green sheet laminate having a state where the cut portion is sandwiched between two dust collection electrodes.

The above plurality of green sheets may simultaneously be laminated, or, for example, the green sheets including the embedded dust collection electrodes are first prepared and then laminated on another green sheet. The laminating is preferably performed while pressurizing.

In the above manufacturing method of the particulate matter detection device of the present invention, desirable electrodes and the like are arranged on a plurality of green sheets, and the green sheets provided with the electrodes and the like are laminated, dried and fired to manufacture the particulate matter detection device, whereby the particulate matter detection device of the present invention can efficiently be manufactured.

[3-3] Firing:

Next, the green sheet laminate is dried and fired to obtain the particulate matter detection device. Further specifically, the obtained green sheet laminate is dried at 60 to 150° C., and fired at 1200 to 1600° C. to prepare the particulate matter detection device. When the green sheets contain an organic binder, degreasing is preferably performed at 400 to 800° C. before the firing.

EXAMPLES

Hereinafter, the present invention will further specifically be described with respect to examples, but the present invention is not limited to these examples.

Example 1

Preparation of Forming Raw Material

As a dielectric raw material, alumina was used, as a binder, polyvinyl butyral was used, as a plasticizer, di-2-ethyl hexyl phthalate was used, as a dispersant, sorbitan tri-oleate was used, and as a dispersion medium, an organic solvent (xylene:butanol=6:4 (mass ratio)) was used. These materials were put into a pot made of alumina, and mixed, to prepare a slurried forming raw material for preparing a green sheet. Amounts of the raw materials for use were 7 parts by mass of the binder, 3.5 parts by mass of the plasticizer, 1.5 parts by mass of the dispersant and 100 parts by mass of the organic solvent with respect to 100 parts by mass of alumina.

Next, the obtained slurried forming raw material for preparing the green sheet was stirred and defoamed under a reduced pressure, and prepared so as to obtain a viscosity of 4 Pa·s. The viscosity of the slurry was measured with a B-type viscosity meter.

(Forming Processing)

Next, the slurried forming raw material obtained by the above method was formed and processed into a sheet-like shape by use of a doctor blade process. In this case, a green sheet provided with a cut portion was also prepared so that a through hole was formed when the green sheets were laminated. A thickness of the green sheet was set to 250 μm.

On the surface of the obtained green sheet, as shown in FIG. 7 to FIG. 12, a pair of measurement electrodes, dust collection electrodes, wires and lead terminals were formed. As to a conductive paste for forming the electrodes, the wires and the lead terminals to be arranged, to platinum powder, there were added 2-ethyl hexanol as a solvent, polyvinyl butyral as a binder, di-2-ethyl hexyl phthalate as a plasticizer, sorbitan trioleate as a dispersant, alumina as a co-base of the green sheet, and glass frit as a sintering aid. The materials were sufficiently kneaded by using a stone mill and a tri-roll mill, to prepare the conductive paste (in terms of a mass ratio, platinum:alumina:glass frit:2-ethyl hexanol:polyvinyl butyral:di-2-ethyl hexyl phthalate:sorbitan trioleate=80:15:5:50:7:3.5:1).

Moreover, as to a conductive paste for forming heating portions, to tungsten powder, there were added 2-ethyl hexanol as a solvent, polyvinyl butyral as a binder, di-2-ethyl hexyl phthalate as a plasticizer, sorbitan trioleate as a dispersant, alumina as a co-base of the green sheet, and glass frit as a sintering aid. The materials were sufficiently kneaded by using a stone mill and a tri-roll mill, to prepare the conductive paste (in terms of a mass ratio, tungsten:alumina:glass frit:2-ethyl hexanol:polyvinyl butyral:di-2-ethyl hexyl phthalate:sorbitan trioleate=75.5:15:5:50:7:3.5:1).

The electrodes, a ground electrode, the wires, the lead terminals and the heating portions were formed through screen printing by use of the pastes obtained by the above processes. In Example 1, each measurement electrode was formed so that seven combteeth portions each having a width of 200 μm and a length of 6 mm were connected to one another by a comb spine portion having a width of 200 μm and a length of 4.5 mm at one end of each portion. It is to be noted that a space between adjacent combteeth portions was 150 mm, and a distance between a comb spine portion of one measurement electrode and the tip of each of the combteeth portions of the other measurement electrode was 250 mm. Moreover, a length of the through hole in a longitudinal direction of the device main body was 5 mm, and the comb spine portions of the measurement electrodes were hidden (covered) by walls which formed the through hole.

When the green sheets provided with the electrodes were laminated, the green sheets were pressurized and laminated by using a uniaxial heatable press machine, to obtain an unfired body of the particulate matter detection device including the green sheet laminate.

(Firing)

The obtained green sheet laminate was dried at 120° C., and fired at 1500° C. to prepare the particulate matter detection device. The obtained particulate matter detection device had such a shape that the other end thereof had a smaller size as shown in FIG. 6B in a rectangular parallelepiped body having a size of 0.7 cm×0.2 cm×12 cm. The other end having the smaller size had a width of 4.25 cm and a length of 1.2 cm.

(Preparation of Particulate Matter Detection Device)

The obtained particulate matter detection device was electrically connected to LCR meter 4263B manufactured by Agilent Technologies Inc. as characteristics measurement means and particulate matter amount calculation means, to measure an electrostatic capacity between the pair of measurement electrodes, thereby detecting a particulate matter.

(Measurement of Particulate Matter)

The particulate matter was detected by using the particulate matter detection device of Example 1 obtained in this manner. Specifically, in an exhaust gas pipe of a 2.2 L diesel engine, a broken DPF having a cylindrical shape with a diameter of 22 mm was installed, and further on a downstream side of the DPF, the particulate matter detection device of Example 1 was installed. As the diesel engine, a direct-jet diesel engine was used, to generate an exhaust gas on operation conditions including a rotation number of 1500 rpm, a torque of 20 N·m, an exhaust gas recirculation (EGR) open degree of 50%, an exhaust gas temperature of 200° C., and suction air of 1.3 m$^3$ (in terms of room temperature)/min.

Figure 13:
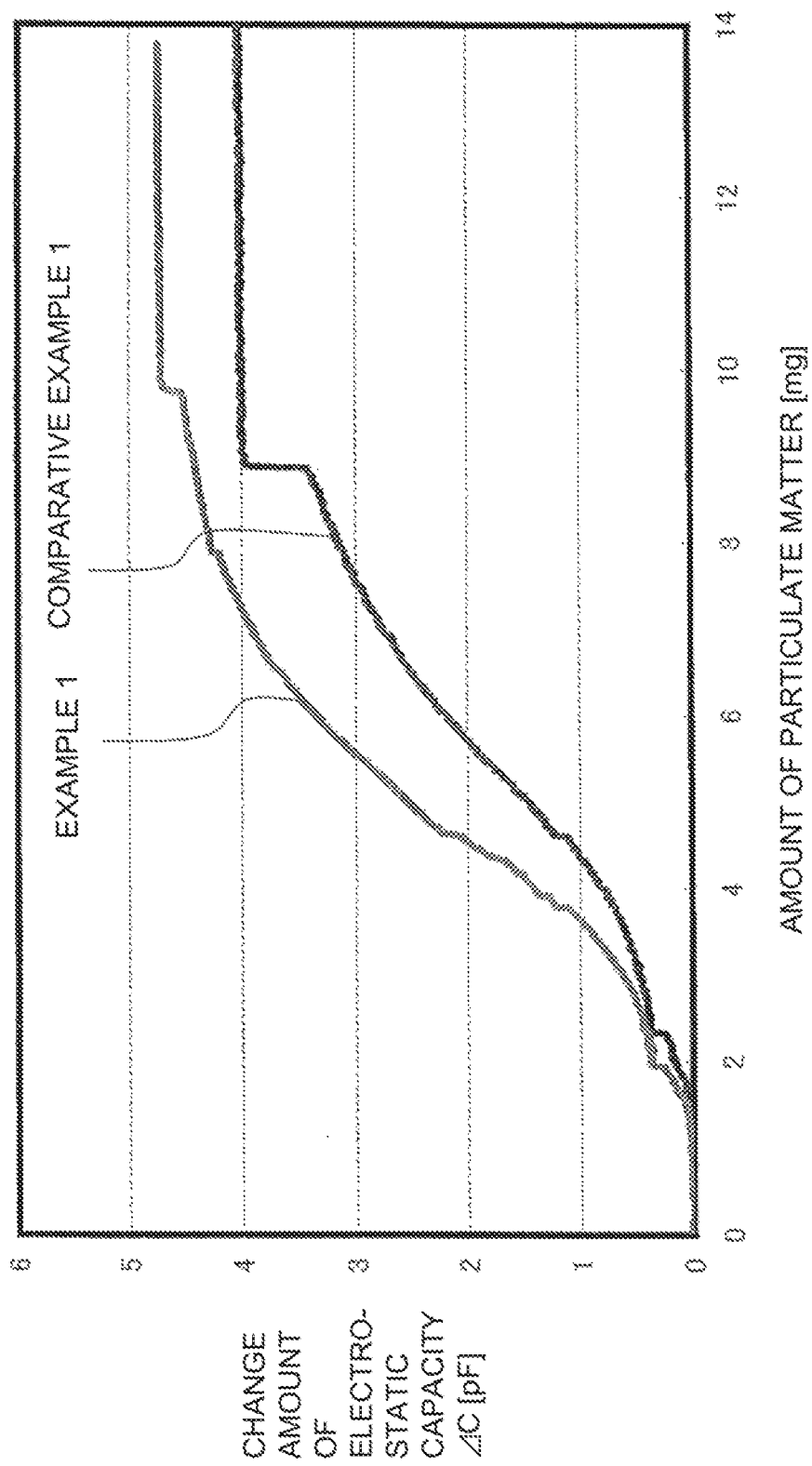
FIG. 13 is a graph showing a relation between a change amount ($\Delta C$ [pF]) of an electrostatic capacity and an amount [mg] of a particulate matter measured by the particulate matter detection device.

It is to be noted that an amount [mg] of the particulate matter in the exhaust gas was simultaneously measured with a smoke meter (trade name: model 4158 manufactured by AVL Corp.). A relation between a change amount ($\Delta C$ [pF]) of the electrostatic capacity and the amount [mg] of the particulate matter measured by the particulate matter detection device of Example 1 is shown in FIG. 13. FIG. 13 is a graph showing the relation between the change amount ($\Delta C$ [pF]) of the electrostatic capacity and the amount [mg] of the particulate matter measured by the particulate matter detection device of Example 1, the abscissa indicates the amount [mg] of the particulate matter, and the ordinate indicates the change amount ($\Delta C$ [pF]) of the electrostatic capacity.

Comparative Example 1

A particulate matter detection device of Comparative Example 1 was prepared in the same manner as in Example 1 except that a length of a through hole in a longitudinal direction of a device main body was 5 mm and a comb spine portion of each measurement electrode was not hidden by walls of the through hole and was disposed in the through hole.

A particulate matter was measured by using the obtained particulate matter detection device of Comparative Example 1 by a method similar to Example 1. A relation between a change amount ($\Delta C$ [pF]) of an electrostatic capacity and the amount [mg] of the particulate matter measured by the particulate matter detection device of Comparative Example 1 is shown in FIG. 13.

(Result)

As shown in FIG. 13, in the particulate matter detection device of Example 1, it has been found that when the same amount of the particulate matter is detected, the change amount ($\Delta C$ [pF]) of the electrostatic capacity is large, and a measurement sensitivity and a measurement accuracy enhance. That is, in the particulate matter detection device of Example 1, the distance between the pair of measurement electrodes is short. Therefore, when the fixed amount of the particulate matter adheres to and around the measurement electrodes, the change of electric characteristics measured between the measurement electrodes is large, and the device has an excellent resolution.

INDUSTRIAL APPLICABILITY

A particulate matter detection device of the present invention can preferably be utilized to immediately detect the generation of a defect of a DPF, thereby recognizing the abnormality of the device, which can contribute to the prevention of air pollution.

DESCRIPTION OF REFERENCE NUMERALS

11: element base material, 12: pair of measurement electrodes, 12a and 12b: measurement electrode, 13: combteeth portion, 14: comb spine portion, 15: comb spine covering portion, 16, 16a and 16b: measurement wire, 17a and 17b: measurement lead terminal, 18: electrode protective film, 20: characteristics measurement means, 21: particulate matter amount calculation means, 31: device main body, 31a: one end, 31b: the other end, 31c: one tip portion, 31d: the other tip portion, 32: through hole, 41: dust collection electrode (high-voltage dust collection electrode), 42: dust collection electrode (ground dust collection electrode), 41a and 42a: dust collection lead terminal, 41b and 42b: dust collection wire, 43: heating portion, 43a: heating lead terminal, 43b: heating wire, and 100, 101, 102, 103, 104 and 105: particulate matter detection device.

What is claimed is:

1. A particulate matter detection device comprising: a plate-like element base material; a pair of measurement electrodes arranged in the element base material; characteristics measurement means for measuring electric characteristics between the pair of measurement electrodes; and particulate matter amount calculation means for obtaining an amount of a particulate matter collected in and around the pair of measurement electrodes on the basis of a change amount of the electric characteristics measured by the characteristics measurement means, wherein the measurement electrodes constituting the pair of measurement electrodes are combteeth-like electrodes each including a plurality of planarly arranged combteeth portions, and a comb spine portion which connects the plurality of combteeth portions of each of the measurement electrodes to one another at one end of each of the plurality of combteeth portions, the combteeth portions of the measurement electrodes are arranged to engage with each other with a space being left therebetween, and a comb spine covering portion made of a dielectric material covers the comb spine portion of at least one of the measurement electrodes without extending over at least part of the surfaces of the plurality of combteeth portions of the pair of measurement electrodes wherein the element base material is a device main body which includes at least one through hole formed in one end thereof and which is elongated in one direction, and the pair of measurement electrodes are arranged on an inner side surface of one wall which forms the through hole or in the wall, and the comb spine covering portion is formed by a wall extending vertically from the wall on which the pair of measurement electrodes are arranged, among the walls which form the through hole.

2. The particulate matter detection device according to claim 1, wherein the comb spine covering portion covers the comb spine portion of the one measurement electrode as well as a tip portion of each of the combteeth portions of the other measurement electrode arranged to engage with each other with the space being left therebetween.

3. The particulate matter detection device according to claim 1, wherein the comb spine covering portion covers the comb spine portion of the one measurement electrode so that the comb spine covering portion abuts on a tip portion of each of the combteeth portions of the other measurement electrode arranged so as to engage with each other with the space being left therebetween.

4. The particulate matter detection device according to claim 1, wherein the measurement electrodes are arranged so that a direction in which combteeth of the combteeth portions of the measurement electrodes extend is orthogonal to a direction in which the through hole extends through the element base material.

5. The particulate matter detection device according to claim 1, wherein a gas including the particulate matter as a detection target is passed through the measurement electrodes in a direction which is orthogonal to the direction in which the combteeth of the combteeth portions of the measurement electrodes extend, to detect the particulate matter.

6. A particulate matter detection device comprising: a plate-like element base material; a pair of measurement electrodes arranged in the element base material; characteristics measurement means for measuring electric characteristics between the pair of measurement electrodes; and particulate matter amount calculation means for obtaining an amount of a particulate matter collected in and around the pair of measurement electrodes on the basis of a change amount of the electric characteristics measured by the characteristics measurement means, wherein the measurement electrodes constituting the pair of measurement electrodes are combteeth-like electrodes each including a plurality of planarly arranged combteeth portions, and a comb spine portion which connects the plurality of combteeth portions of each of the measurement electrodes to one another at one end of each of the plurality of combteeth portions, the combteeth portions of the measurement electrodes are arranged to engage with each other with a space being left therebetween, and the comb spine portion of at least one of the measurement electrodes is covered with a comb spine covering portion made of a dielectric material, and at least part of the surfaces of the pair of measurement electrodes is covered with an electrode protective film having a smaller thickness than the comb spine covering portion.

7. The particulate matter detection device according to claim 6, wherein the comb spine covering portion covers the comb spine portion of the one measurement electrode as well as a tip portion of the each of the combteeth portions of the other measurement electrode arranged to engage with each other with the space being left therebetween.

8. The particulate matter detection device according to claim 6, wherein the comb spine covering portion covers the comb spine portion of the one measurement electrode so that the comb spine covering portion abuts on a tip portion of each of the combteeth portions of the other measurement electrode arranged so as to engage with each other with the space being left therebetween.

9. The particulate matter detection device according to claim 6, wherein the element base material is a device main body which includes at least one through hole formed in one end thereof and which is elongated in one direction, and the pair of measurement electrodes are arranged on an inner side surface of one wall which forms the through hole or in the wall, and the comb spine covering portion is formed by a wall extending vertically from the wall on which the pair of measurement electrodes are arranged, among the walls which form the through hole.

10. The particulate matter detection device according to claim 9, wherein the measurement electrodes are arranged so that a direction in which combteeth of the combteeth portions of the measurement electrodes extend is orthogonal to a direction in which the through hole extends through the element base material.

11. The particulate matter detection device according to claim 6, wherein a gas including the particulate matter as a detection target is passed through the measurement electrodes in a direction which is orthogonal to the direction in which the combteeth of the combteeth portions of the measurement electrodes extend, to detect the particulate matter.

* * * * *